US009719993B2

(12) United States Patent
Dalmau

(10) Patent No.: US 9,719,993 B2
(45) Date of Patent: Aug. 1, 2017

(54) DIAGNOSTIC METHOD FOR DETECTING AN AUTOIMMUNE DISEASE

(71) Applicants: INSTITUCIÓ CATALANA DE RECERCA I ESTUDIS AVANÇATS, Barcelona (ES); INSTITUT D'INVESTIGACIONES BIOMÈDIQUES AUGUST PI I SUNYER, Barcelona (ES)

(72) Inventor: Josep Dalmau, Barcelona (ES)

(73) Assignees: INSTITUCIÓ CATALANA DE RECERCA I ESTUDIS AVANÇATS, Barcelona (ES); INSTITUT D'INVESTIGACIONES BIOMÈDIQUES AUGUST PI I SUNYER, Barcelona (ES)

( * ) Notice: Subject to any disclaimer, the term of this patent is extended or adjusted under 35 U.S.C. 154(b) by 70 days.

(21) Appl. No.: 14/427,129

(22) PCT Filed: Sep. 11, 2013

(86) PCT No.: PCT/EP2013/068845
§ 371 (c)(1),
(2) Date: Mar. 10, 2015

(87) PCT Pub. No.: WO2014/041035
PCT Pub. Date: Mar. 20, 2014

(65) Prior Publication Data
US 2015/0247847 A1    Sep. 3, 2015

(30) Foreign Application Priority Data

Sep. 11, 2012 (EP) .................................... 12183919
Sep. 11, 2012 (EP) .................................... 12380048

(51) Int. Cl.
| G01N 33/564 | (2006.01) |
| G01N 33/68 | (2006.01) |
| A61K 39/00 | (2006.01) |
| C07K 14/705 | (2006.01) |
| C12N 9/48 | (2006.01) |
| A61L 31/10 | (2006.01) |
| A61M 1/36 | (2006.01) |
| A61K 38/00 | (2006.01) |

(52) U.S. Cl.
CPC ....... *G01N 33/564* (2013.01); *A61K 39/0008* (2013.01); *A61L 31/10* (2013.01); *A61M 1/3621* (2013.01); *A61M 1/3687* (2013.01); *C07K 14/705* (2013.01); *C12N 9/485* (2013.01); *G01N 33/6893* (2013.01); *A61K 38/00* (2013.01); *C07K 2319/22* (2013.01); *C07K 2319/41* (2013.01); *C07K 2319/43* (2013.01); *C07K 2319/60* (2013.01); *C07K 2319/61* (2013.01); *G01N 2333/705* (2013.01)

(58) Field of Classification Search
CPC ............. G01N 33/564; G01N 33/6893; G01N 2333/705; A61K 39/0008; C07K 14/705
See application file for complete search history.

(56) References Cited

U.S. PATENT DOCUMENTS

2011/0250287 A1    10/2011    Bristow

FOREIGN PATENT DOCUMENTS

| EP | 1 279 744 A2 | 1/2003 |
| WO | 00/67796 A1 | 11/2000 |
| WO | 03/016475 A2 | 2/2003 |
| WO | 2005/108997 A1 | 11/2005 |

OTHER PUBLICATIONS

Boronat et al., "Encephalitis and antibodies to DPPX, a subunit of Kv4.2 potassium channels," *Ann Neurol.* 73(1):120-128, Jan. 2013.
Boronat et al., "WIP1802: Encephalitis and Antibodies to DPPX, a Regulatory Subunit of Kv4.2 Potassium Channels," 137th Annual Meeting of the American Neurological Association; Boston, MA, Oct. 7-10, 2012, p. S131.
European Search Report and Written Opinion dated Feb. 1, 2013, for corresponding EP Application No. 12183919.5, 7 pages.
European Search Report and Written Opinion dated Apr. 10, 2013, for corresponding EP Application No. 12380048.4, 7 pages.
International Search Report mailed Nov. 4, 2013, for corresponding International Application No. PCT/EP2013/068845, 4 pages.
Irani et al., "Antibodies to Kv 1 potassium channel-complex proteins leucine-rich, glioma inactivated 1 protein and contactin-associated protein-2 in limbic encephalitis, Morvan's syndrome and acquired neuromyotonia," *Brain* 133:2734-2748, 2010.
Lai et al., "Investigation of LGI1 as the antigen in limbic encephalitis previously attributed to potassium channels: a case series," *Lancet Neurol.* 9(8):776-785, Aug. 2010.
Lancaster et al., "Encephalitis and antibodies to synaptic and neuronal cell surface proteins," *Neurology* 77:179-189, Jul. 12, 2011.
Universal Protein Resource, "Dipeptidyl aminopeptidase-like protein 6," Sequence ID: P46101-DPP6_RAT, retrieved from http://www.uniprot.org/uniprot/P46101 on Sep. 14, 2015, 10 pages.

(Continued)

*Primary Examiner* — Ruixiang Li
(74) *Attorney, Agent, or Firm* — Seed IP Law Group LLP

(57) ABSTRACT

The present invention relates to a polypeptide or protein for use in a method of diagnosis or treatment of an autoimmune disease in a subject, characterized in that said polypeptide or protein comprises one or more epitopes derived from the protein DPPX. Further, the invention relates to a nucleic acid or vector encoding such polypeptide, to a cell comprising such a vector, to an in vitro diagnostic method and test kit involving such polypeptide, to a pharmaceutical composition comprising such polypeptide, to a medical device coated with such polypeptide or pharmaceutical composition and to methods for treating an autoimmune disease in a subject.

13 Claims, 8 Drawing Sheets

(56) References Cited

OTHER PUBLICATIONS

Wada et al., "Differential expression of two distinct forms of mRNA encoding members of a dipeptidyl aminopeptidase family," *Proc. Natl. Acad. Sci. USA* 89:197-201, Jan. 1992.

SEQUENCE LISTING

```
<160> NUMBER OF SEQ ID NOS: 4

<210> SEQ ID NO 1
<211> LENGTH: 801
<212> TYPE: PRT
<213> ORGANISM: Homo sapiens
<220> FEATURE:
<221> NAME/KEY: SOURCE
<222> LOCATION: 1..801
<223> OTHER INFORMATION: /mol_type="protein"
      /organism="Homo sapiens"

<400> SEQUENCE: 1

Met Lys Glu Lys Ala Met Ile Lys Thr Ala Lys Met Gln Gly Asn Val
1               5                   10                  15

Met Glu Leu Val Gly Ser Asn Pro Pro Gln Arg Asn Trp Lys Gly Ile
            20                  25                  30

Ala Ile Ala Leu Leu Val Ile Leu Val Ile Cys Ser Leu Ile Val Thr
        35                  40                  45

Ser Val Ile Leu Leu Thr Pro Ala Glu Asp Asn Ser Leu Ser Gln Lys
    50                  55                  60

Lys Lys Val Thr Val Glu Asp Leu Phe Ser Glu Asp Phe Lys Ile His
65                  70                  75                  80

Asp Pro Glu Ala Lys Trp Ile Ser Asp Thr Glu Phe Ile Tyr Arg Glu
                85                  90                  95

Gln Lys Gly Thr Val Arg Leu Trp Asn Val Glu Thr Asn Thr Ser Thr
```

-continued

```
              100                 105                 110
Val Leu Ile Glu Gly Lys Lys Ile Glu Ser Leu Arg Ala Ile Arg Tyr
            115                 120                 125
Glu Ile Ser Pro Asp Arg Glu Tyr Ala Leu Phe Ser Tyr Asn Val Glu
130                 135                 140
Pro Ile Tyr Gln His Ser Tyr Thr Gly Tyr Tyr Val Leu Ser Lys Ile
145                 150                 155                 160
Pro His Gly Asp Pro Gln Ser Leu Asp Pro Pro Glu Val Ser Asn Ala
                165                 170                 175
Lys Leu Gln Tyr Ala Gly Trp Gly Pro Lys Gly Gln Gln Leu Ile Phe
            180                 185                 190
Ile Phe Glu Asn Asn Ile Tyr Tyr Cys Ala His Val Gly Lys Gln Ala
        195                 200                 205
Ile Arg Val Val Ser Thr Gly Lys Glu Gly Val Ile Tyr Asn Gly Leu
    210                 215                 220
Ser Asp Trp Leu Tyr Glu Glu Ile Leu Lys Thr His Ile Ala His
225                 230                 235                 240
Trp Trp Ser Pro Asp Gly Thr Arg Leu Ala Tyr Ala Ala Ile Asn Asp
                245                 250                 255
Ser Arg Val Pro Ile Met Glu Leu Pro Thr Tyr Thr Gly Ser Ile Tyr
            260                 265                 270
Pro Thr Val Lys Pro Tyr His Tyr Pro Lys Ala Gly Ser Glu Asn Pro
        275                 280                 285
Ser Ile Ser Leu His Val Ile Gly Leu Asn Gly Pro Thr His Asp Leu
    290                 295                 300
Glu Met Met Pro Pro Asp Asp Pro Arg Met Arg Glu Tyr Tyr Ile Thr
305                 310                 315                 320
Met Val Lys Trp Ala Thr Ser Thr Lys Val Ala Val Thr Trp Leu Asn
                325                 330                 335
Arg Ala Gln Asn Val Ser Ile Leu Thr Leu Cys Asp Ala Thr Thr Gly
            340                 345                 350
Val Cys Thr Lys Lys His Glu Asp Glu Ser Glu Ala Trp Leu His Arg
        355                 360                 365
Gln Asn Glu Glu Pro Val Phe Ser Lys Asp Gly Arg Lys Phe Phe Phe
    370                 375                 380
Ile Arg Ala Ile Pro Gln Gly Gly Arg Gly Lys Phe Tyr His Ile Thr
385                 390                 395                 400
Val Ser Ser Ser Gln Pro Asn Ser Ser Asn Asp Asn Ile Gln Ser Ile
                405                 410                 415
Thr Ser Gly Asp Trp Asp Val Thr Lys Ile Leu Ala Tyr Asp Glu Lys
            420                 425                 430
Gly Asn Lys Ile Tyr Phe Leu Ser Thr Glu Asp Leu Pro Arg Arg Arg
        435                 440                 445
Gln Leu Tyr Ser Ala Asn Thr Val Gly Asn Phe Asn Arg Gln Cys Leu
    450                 455                 460
Ser Cys Asp Leu Val Glu Asn Cys Thr Tyr Phe Ser Ala Ser Phe Ser
465                 470                 475                 480
His Ser Met Asp Phe Phe Leu Leu Lys Cys Glu Gly Pro Gly Val Pro
                485                 490                 495
Met Val Thr Val His Asn Thr Thr Asp Lys Lys Met Phe Asp Leu
            500                 505                 510
Glu Thr Asn Glu His Val Lys Lys Ala Ile Asn Asp Arg Gln Met Pro
        515                 520                 525
```

```
Lys Val Glu Tyr Arg Asp Ile Glu Ile Asp Asp Tyr Asn Leu Pro Met
            530                 535                 540

Gln Ile Leu Lys Pro Ala Thr Phe Thr Asp Thr Thr His Tyr Pro Leu
545                 550                 555                 560

Leu Leu Val Val Asp Gly Thr Pro Gly Ser Gln Ser Val Ala Glu Lys
            565                 570                 575

Phe Glu Val Ser Trp Glu Thr Val Met Val Ser Ser His Gly Ala Val
            580                 585                 590

Val Val Lys Cys Asp Gly Arg Gly Ser Gly Phe Gln Gly Thr Lys Leu
            595                 600                 605

Leu His Glu Val Arg Arg Arg Leu Gly Leu Leu Glu Glu Lys Asp Gln
            610                 615                 620

Met Glu Ala Val Arg Thr Met Leu Lys Glu Gln Tyr Ile Asp Arg Thr
625                 630                 635                 640

Arg Val Ala Val Phe Gly Lys Asp Tyr Gly Gly Tyr Leu Ser Thr Tyr
            645                 650                 655

Ile Leu Pro Ala Lys Gly Glu Asn Gly Gln Thr Phe Thr Cys Gly
            660                 665                 670

Ser Ala Leu Ser Pro Ile Thr Asp Phe Lys Leu Tyr Ala Ser Ala Phe
            675                 680                 685

Ser Glu Arg Tyr Leu Gly Leu His Gly Leu Asp Asn Arg Ala Tyr Glu
            690                 695                 700

Met Thr Lys Val Ala His Arg Val Ser Ala Leu Glu Glu Gln Gln Phe
705                 710                 715                 720

Leu Ile Ile His Pro Thr Ala Asp Glu Lys Ile His Phe Gln His Thr
            725                 730                 735

Ala Glu Leu Ile Thr Gln Leu Ile Arg Gly Lys Ala Asn Tyr Ser Leu
            740                 745                 750

Gln Ile Tyr Pro Asp Glu Ser His Tyr Phe Thr Ser Ser Leu Lys
            755                 760                 765

Gln His Leu Tyr Arg Ser Ile Ile Asn Phe Phe Val Glu Cys Phe Arg
            770                 775                 780

Ile Gln Asp Lys Leu Leu Thr Val Thr Ala Lys Glu Asp Glu Glu
785                 790                 795                 800

Asp

<210> SEQ ID NO 2
<211> LENGTH: 748
<212> TYPE: PRT
<213> ORGANISM: Rattus norvegicus
<220> FEATURE:
<221> NAME/KEY: SOURCE
<222> LOCATION: 1..748
<223> OTHER INFORMATION: /mol_type="protein"
    /organism="Rattus norvegicus"

<400> SEQUENCE: 2

Thr Pro Ala Glu Asp Thr Ser Leu Ser Gln Lys Lys Val Thr Val
1               5                   10                  15

Glu Asp Leu Phe Ser Glu Asp Phe Lys Ile His Asp Pro Glu Ala Lys
            20                  25                  30

Trp Ile Ser Asp Lys Glu Phe Ile Tyr Arg Glu Arg Lys Gly Ser Val
        35                  40                  45

Ile Leu Arg Asn Val Glu Thr Asn Asn Ser Thr Val Leu Ile Glu Gly
    50                  55                  60
```

```
Lys Lys Ile Glu Ser Leu Arg Ala Ile Arg Tyr Glu Ile Ser Pro Asp
 65                  70                  75                  80

Lys Glu Tyr Ala Leu Phe Ser Tyr Asn Val Glu Pro Val Tyr Gln His
                 85                  90                  95

Ser His Thr Gly Tyr Tyr Val Leu Ser Lys Ile Pro His Gly Asp Pro
            100                 105                 110

Gln Ser Leu Asp Pro Pro Glu Val Ser Asn Ala Lys Leu Gln Tyr Ala
        115                 120                 125

Gly Trp Gly Pro Lys Gly Gln Gln Leu Ile Phe Ile Phe Glu Asn Asn
    130                 135                 140

Ile Tyr Tyr Cys Ala His Val Gly Lys Gln Ala Ile Arg Val Val Ser
145                 150                 155                 160

Thr Gly Lys Glu Gly Val Ile Tyr Asn Gly Leu Ser Asp Trp Leu Tyr
                165                 170                 175

Glu Glu Glu Ile Leu Lys Ser His Ile Ala His Trp Trp Ser Pro Asp
            180                 185                 190

Gly Thr Arg Leu Ala Tyr Ala Thr Ile Asn Asp Ser Arg Val Pro Leu
        195                 200                 205

Met Glu Leu Pro Thr Tyr Thr Gly Ser Val Tyr Pro Thr Val Lys Pro
    210                 215                 220

Tyr His Tyr Pro Lys Ala Gly Ser Glu Asn Pro Ser Ile Ser Leu His
225                 230                 235                 240

Val Ile Gly Leu Asn Gly Pro Thr His Asp Leu Glu Met Met Pro Pro
                245                 250                 255

Asp Asp Pro Arg Met Arg Glu Tyr Tyr Ile Thr Met Val Lys Trp Ala
            260                 265                 270

Thr Ser Thr Lys Val Ala Val Thr Trp Leu Asn Arg Ala Gln Asn Val
        275                 280                 285

Ser Ile Leu Thr Leu Cys Asp Ala Thr Thr Gly Val Cys Thr Lys Lys
    290                 295                 300

His Glu Asp Glu Ser Glu Ala Trp Leu His Arg Gln Asn Glu Glu Pro
305                 310                 315                 320

Val Phe Ser Lys Asp Gly Arg Lys Phe Phe Val Arg Ala Ile Pro
                325                 330                 335

Gln Gly Gly Arg Gly Lys Phe Tyr His Ile Thr Val Ser Ser Ser Gln
            340                 345                 350

Pro Asn Ser Ser Asn Asp Asn Ile Gln Ser Ile Thr Ser Gly Asp Trp
        355                 360                 365

Asp Val Thr Glu Ile Leu Thr Tyr Asp Glu Lys Arg Asn Lys Leu Tyr
    370                 375                 380

Phe Leu Ser Thr Glu Asp Leu Pro Arg Arg His Leu Tyr Ser Ala
385                 390                 395                 400

Asn Thr Val Asp Asp Phe Asn Arg Gln Cys Leu Ser Cys Asp Leu Val
                405                 410                 415

Glu Asn Cys Thr Tyr Val Ser Ala Ser Phe Ser His Asn Met Asp Phe
            420                 425                 430

Phe Leu Leu Lys Cys Glu Gly Pro Gly Val Pro Thr Val Thr Val His
        435                 440                 445

Asn Thr Thr Asp Lys Arg Arg Met Phe Asp Leu Glu Ala Asn Glu Gln
    450                 455                 460

Val Gln Lys Ala Ile Tyr Asp Arg Gln Met Pro Lys Ile Glu Tyr Arg
465                 470                 475                 480

Lys Ile Glu Val Glu Asp Tyr Ser Leu Pro Met Gln Ile Leu Lys Pro
```

```
                        485                 490                 495
Ala Thr Phe Thr Asp Thr Ala His Tyr Pro Leu Leu Val Val Asp
                500                 505                 510
Gly Thr Pro Gly Ser Gln Ser Val Ser Glu Arg Phe Glu Val Thr Trp
            515                 520                 525
Glu Thr Val Leu Val Ser Ser His Gly Ala Val Val Lys Cys Asp
            530                 535                 540
Gly Arg Gly Ser Gly Phe Gln Gly Thr Lys Leu Leu His Glu Val Arg
545                 550                 555                 560
Arg Arg Leu Gly Phe Leu Glu Glu Lys Asp Gln Met Glu Ala Val Arg
                565                 570                 575
Thr Met Leu Lys Glu Gln Tyr Ile Asp Lys Thr Arg Val Ala Val Phe
                580                 585                 590
Gly Lys Asp Tyr Gly Gly Tyr Leu Ser Thr Tyr Ile Leu Pro Ala Lys
                595                 600                 605
Gly Glu Asn Gln Gly Gln Thr Phe Thr Cys Gly Ser Ala Leu Ser Pro
                610                 615                 620
Ile Thr Asp Phe Lys Leu Tyr Ala Ser Ala Phe Ser Glu Arg Tyr Leu
625                 630                 635                 640
Gly Leu His Gly Leu Asp Asn Arg Ala Tyr Glu Met Thr Lys Leu Ala
                645                 650                 655
His Arg Val Ser Ala Leu Glu Asp Gln Gln Phe Leu Ile Ile His Ala
                660                 665                 670
Thr Ala Asp Glu Lys Ile His Phe Gln His Thr Ala Glu Leu Ile Thr
                675                 680                 685
Gln Leu Ile Lys Gly Lys Ala Asn Tyr Ser Leu Gln Ile Tyr Pro Asp
            690                 695                 700
Glu Ser His Tyr Phe His Ser Val Ala Leu Lys Gln His Leu Tyr Arg
705                 710                 715                 720
Ser Ile Ile Gly Phe Phe Val Glu Cys Phe Arg Ile Gln Asp Lys Leu
                725                 730                 735
Pro Thr Ala Thr Ala Lys Glu Asp Glu Glu Asp
                740                 745

<210> SEQ ID NO 3
<211> LENGTH: 111
<212> TYPE: PRT
<213> ORGANISM: Rattus norvegicus
<220> FEATURE:
<221> NAME/KEY: SOURCE
<222> LOCATION: 1..111
<223> OTHER INFORMATION: /mol_type="protein"
      /organism="Rattus norvegicus"

<400> SEQUENCE: 3

Met Ala Ser Leu Tyr Gln Arg Phe Thr Gly Lys Ile Asn Thr Ser Arg
1               5                   10                  15
Ser Phe Pro Ala Pro Glu Ala Ser His Leu Leu Gly Gly Gln Gly
            20                  25                  30
Pro Glu Glu Asp Ala Gly Ser Lys Pro Leu Gly Pro Gln Ala Gln Ala
            35                  40                  45
Val Ala Pro Arg Glu Arg Gly Gly Ala Gly Gly Arg Pro Arg Phe Gln
            50                  55                  60
Tyr Gln Ala Arg Ser Asp Cys Asp Glu Glu Asp Glu Leu Val Gly Ser
65              70                  75                  80
Asn Pro Pro Gln Arg Asn Trp Lys Gly Ile Ala Ile Ala Leu Leu Val
```

```
                    85                  90                  95
Ile Leu Val Ile Cys Ser Leu Ile Val Thr Ser Val Ile Leu Leu
                100                 105                 110

<210> SEQ ID NO 4
<211> LENGTH: 55
<212> TYPE: PRT
<213> ORGANISM: Rattus norvegicus
<220> FEATURE:
<221> NAME/KEY: SOURCE
<222> LOCATION: 1..55
<223> OTHER INFORMATION: /mol_type="protein"
      /organism="Rattus norvegicus"

<400> SEQUENCE: 4

Met Thr Thr Ala Lys Glu Pro Ser Ala Ser Gly Lys Ser Val Gln Gln
1               5                   10                  15

Gln Asp Gln Glu Leu Val Gly Ser Asn Pro Pro Gln Arg Asn Trp Lys
                20                  25                  30

Gly Ile Ala Ile Ala Leu Leu Val Ile Leu Val Ile Cys Ser Leu Ile
            35                  40                  45

Val Thr Ser Val Ile Leu Leu
    50                  55
```

DIAGNOSTIC METHOD FOR DETECTING AN AUTOIMMUNE DISEASE

FIELD OF THE INVENTION

The present invention relates to the diagnosis and treatment of a newly identified autoimmune disorder, providing a polypeptide or protein comprising at least one epitope derived from a novel cell-surface autoantigen and associated means and methods for detection and treatment of said autoimmune disorder.

BACKGROUND OF THE INVENTION

The discovery that memory, behavior, cognition, and thought processes can be altered by autoantibodies has changed the approach to the diagnosis and treatment of neuropsychiatric disorders previously considered idiopathic. Since 2007, seven such antibodies have been identified (anti-NMDAR, AMPAR, GABA(B), LGI1, Caspr2, GluR, and mGluR5), all targeting cell surface proteins involved in synaptic transmission, plasticity, or nerve excitability, and associated with syndromes that although severe, often respond to immunotherapy.[1] Patients may be comatose for several months, with bizarre behaviors, abnormal movements, or refractory seizures and still recover with immunotherapy and extended care support.[2] Considering that until recently these disorders were unknown, the relative high frequency of some has been surprising. For example, in a center focused in the diagnosis and epidemiology of encephalitis (California Encephalitis Project) the frequency of anti-NMDAR encephalitis surpassed that of any individual viral encephalitis.[3] For these reasons, similar immune mechanisms are increasingly being considered in patients who develop rapidly progressive neuropsychiatric symptoms in the context of encephalitis of unknown etiology, a situation that occurs frequently. Nowadays about 70% of encephalitis of unclear etiology remain undiagnosed after extensive evaluation for infectious etiologies.[4] In this setting, the identification of autoantibodies against neuronal cell surface antigens shifts the management to the use of immunotherapy and may extend the intensive care support in cases that otherwise might be considered futile.

In view of the above, the problem underlying the present invention resides in providing means for diagnosis and treatment of a previously unidentified autoimmune encephalitis, or encephalitis of unknown etiology, respectively.

SUMMARY OF THE INVENTION

This problem is solved by the subject of the claims, in particular by providing a polypeptide or protein comprising at least one epitope derived from DPPX, a novel autoantigen for detection and treatment of autoimmune disorder, in particular encephalitis, to a nucleic acid or vector encoding such polypeptide, to a cell comprising such a vector, to an in vitro diagnostic method and test kit involving such polypeptide, to a pharmaceutical composition comprising such polypeptide, to a medical device coated with such polypeptide or pharmaceutical composition and to methods for treating an autoimmune disorder, in particular encephalitis, in a subject.

One advantage of the present invention resides in the fact that diagnosis of encephalitis of unknown etiology enables identification of the disease as autoimmune encephalitis, distinction from other (non-autoimmune) forms of encephalitis or other diseases or related symptoms, respectively, and thus provides for specific treatment of the patients with, for example, immunosuppressive agents.

DETAILED DESCRIPTION OF THE INVENTION

Figure 1:
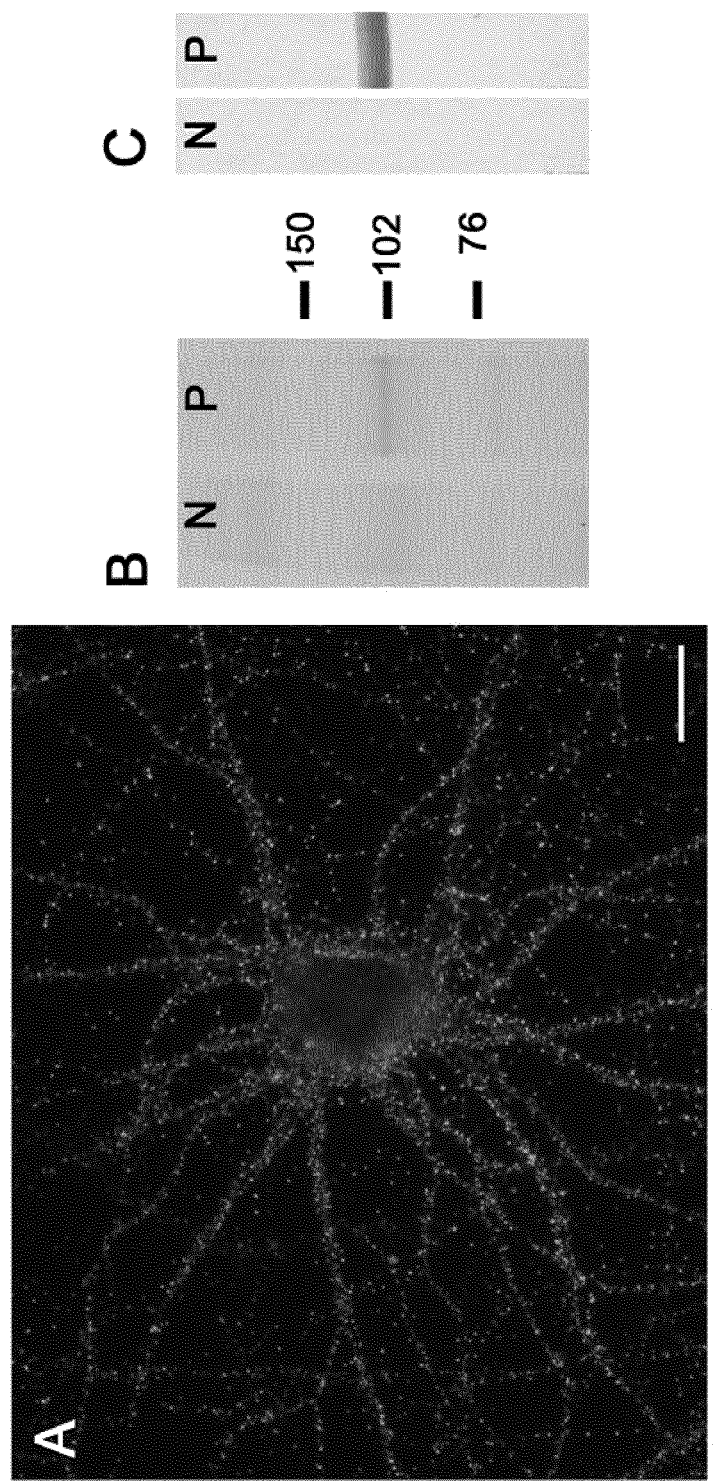
FIG. 1 shows the immunoprecipitation of DPPX.

A "polypeptide", according to the present invention, is understood to be a polymer of two, three, four, five, six, seven or eight or more amino acids, which may include standard amino acids as well as non standard amino acids. The terms polypeptide, peptide and protein are used interchangeably herein.

The term "autoimmune disease", with regard to the present invention relates to diseases that are associated with the emergence of antibodies against DPPX. As reported herein, patients exhibiting such autoimmune disease suffer, for example, from symptoms including seizures, cognitive dysfunction, hallucinations, psychiatric symptoms, agitation, confusion, resting tremor and myoclonus. The majority of these symptoms are associated with a neural disorder. Hence, according to a preferred embodiment of the invention, an autoimmune disease is an autoimmune disease of the nervous system. Moreover, the symptoms listed herein are associated at least in part with defects in the central nervous system. Therefore, according to another embodiment of the invention, the autoimmune disease is autoimmune encephalitis. Still further, a certain set of symptoms, such as tremor, may also be result from defects in the peripheral nervous system, e.g. by autoimmune diseases affecting the motor neurons. Accordingly, according to a further embodiment of the present invention, the autoimmune disease is autoimmune disease of the peripheral nervous system. In addition, severe diarrhea, constipation and weight loss was observed in patients suffering from the diseases described herein, indicating that also other tissues, such as tissues of the digestive tract, may be affected by such autoimmune diseases. Hence, according to an embodiment of the present invention, the autoimmune disease is autoimmune disease of the autonomic nervous system. The terms disorder and disease are used interchangeably herein.

An "epitope", within the scope of the present invention, is understood to be a part of a polypeptide which can be specifically recognized (i.e. bound) by an antibody. The epitope may be a conformational epitope, composed of discontinuous sections of the polypeptide's amino acid sequence, or a linear epitope, composed of a continuous section of polypeptide's amino acid sequence.

The term "derived", with regard to epitopes, within the scope of the present invention relates to epitopes formed from discontinuous or continuous sections of the primary amino acid sequence of a polypeptide or protein. It is known in the art, that one or more amino acids in epitopes may be replaced e.g. by conservative amino acid replacement (e.g. glutamate to aspartate E→D, glutamine to asparagines Q→N, phenylalanine to tyrosine F→Y, leucine to isoleucine L→I) substantially without changing antibody-binding strength or specificity. Accordingly, the term "derived" relates also to such epitopes that, while featuring differences in the amino acid sequence, exhibit an unchanged or substantially unchanged antibody-binding strength or specificity when compared to epitopes with the original amino acid sequence.

"Nucleic acid", according to the present invention, relates to a DNA or RNA polymer including also chemical derivatives thereof or synthetic analogs such as Peptide nucleic acids or Morpholino nucleic acids. It is known in the art that, due to the degeneration of the genetic code, certain changes of the nucleic acid code do not result in changes of the peptide sequence encoded therein. Accordingly, the term "nucleic acid" also encompasses nucleic acid sequences differing in sequence from the original nucleic acid sequences as long as coding for the same peptide sequence.

A "vector" according to the present invention is understood to be a circular or linear nucleic acid sequence including an insert, for example a gene or nucleic acid sequence encoding a desired protein, and other features such as sequences required for vector replication, expression of the insert, positive selection of vector bearing host cells or the expression of marker proteins. Such vectors and sequences are extensively known from the prior art.

A "cell" within the scope of the present invention is any prokaryotic or eukaryotic host cell capable of being transformed with a vector. For example, a cell may be a bacterial cell such as an Escherichia coli cell or a eukaryotic cell such as an immortalized human culture cell. One example for an immortalized human culture cell is a HEK293 cell.

The term "DPPX" relates to dipeptidyl-peptidase-like protein-6 (DPP6 or DPPX), a cell surface auxiliary subunit of the Kv4.2 potassium channels. Synonyms of DPPX include dipeptidylaminopeptidase-related protein, dipeptidyl peptidase 6, dipeptidyl peptidase IV-like protein, and dipeptidyl peptidase VI.

DPPX is highly conserved so that even DPPX from species only distantly related to human is suitable for eliciting specific binding by human anti-DPPX antibodies. This holds true for all human isoforms of the DPPX protein. In addition, it is known that, for example, linear MHC class I epitopes are about 8 to 11 amino acids in length. Hence, in a DPPX homolog already regions of between 8 to 11 amino acids in length, conserved between the respective species and human, are in principle sufficient to elicit specific binding by human anti-DPPX antibodies. In this connection, conserved sequences making up a conformational epitope may be even shorter. Accordingly, "DPPX" with regard to the present invention relates to any known isoforms of the protein DPPX originating from eukaryotes, preferably mammals, more preferably *homo sapiens* or *rattus norvegicus*.

In addition, specific binding by human anti-DPPX antibodies may also be elicited with homologs of DPPX, such as naturally occurring homologs of DPPX. Also included are non-naturally occurring homologs of DPPX such as, homologs derived from naturally occurring DPPX homologs, for example, by deletion or exchange of single or multiple amino acids or even protein motifs or domains. Accordingly, "DPPX" with regard to the present invention relates also to naturally and non-naturally occurring homologs of DPPX.

We herein report 4 patients with a novel autoimmune disorder characterized by subacute development of cognitive dysfunction, agitation, hallucinations, confusion, resting tremor and myoclonus in association with antibodies against DPPX, a cell surface auxiliary subunit of the Kv4.2 potassium channel. In three patients, the neurological symptoms were preceded or overlapped with severe diarrhea and weight loss to the point that two patients underwent extensive endoscopic biopsies without a clear diagnosis. Support for an autoimmune etiology of this disorder is provided by the presence of cerebrospinal (CSF) pleocytosis, increased IgG index or oligoclonal bands, and the neurological response to intensive or persistent immunotherapy. Using patients' antibodies three sets of experiments established DPPX as the main autoantigen: immunoprecipitation of DPPX from cultures of dissociated rat hippocampal neurons; immunostaining of DPPX in a cell-based assay; and comparative brain immunostaining of wild-type and DPPX-null mice, showing abrogation of reactivity of patients' antibodies with the DPPX-null mice brain, and revealing in one patient additional antibodies to an unknown antigen.

DPPX has a critical role "tuning up" the Kv4.2 channels by remodeling channel gating.[5] This type of potassium channel belongs to the mammalian Shal K+ channel family[6] which has different properties compared with the Shaker K+ (Kv1) family, previously considered the target of antibody-associated limbic encephalitis, neuromyotonia, or Morvan's syndrome (the main autoantigens are LGI1 and Caspr2).[7,8] The Kv4.2 channels operate in the subthreshold range of membrane potentials.[5] This somatodendriticsubthreshold A-type K+ current ($I_{SA}$) is a critical component of the ensemble of voltage-gated ionic currents that determine somatodendritic signal integration.[9] In many neurons, action potentials that initiate in the axon hillock propagate down the axon but also backpropagate into the dendrites. In the dendritic tree, these action potentials serve as signals that report the status of the neuron's output. The transient subthreshold $I_{SA}$ current in dendrites attenuates this backpropagation of action potentials. Under resting conditions $I_{SA}$ shuts the action potential as it tries to spread into the distal regions of the dendritic tree. However, when excitatory synaptic inputs and somatic action potentials are paired within a certain time window, the ensuing subthreshold depolarization in distal dendrites inactivates $I_{SA}$, and the attenuation of backpropagating the action potential is substantially reduced.[6] It is believed that this interaction provides a coincidence detection mechanism that plays an important role in dendritic $Ca^{++}$ signaling, signal integration and synaptic plasticity.[5,6,9]

The function of the Kv4 channels is dependent on two auxiliary subunits, the intracellular Kv-channel-interacting proteins (KChIPs),[10] and the extracellular DPPX that is predominantly expressed in hippocampal pyramidal neurons and cerebellum, or DPP10 that has a different brain expression profile and is also present in pancreas.[11,12] DPPX is composed of a short cytoplasmic N-terminus, a single transmembrane domain, and a large extracellular C-terminus. Depending on the length of the cytoplasmic domain, two adult forms, DPPX-S and DPPX-L, have been identified.[13,14] Consistent with the presence of antibodies against extracellular epitopes, our 4 patients' serum and CSF equally recognized DPPX-S and DPPX-L, but two patients had additional antibodies against intracellular epitopes present in a mutant construct in which the extracellular C-terminus was deleted.

The extensive evaluation and prolonged follow-up of three patients indicate that this disorder is severe, resulting in lengthy hospitalizations or multiple relapses that usually occurred while the immunotherapy was decreased. Patient #1 was able to return home 15 months after symptom onset, and had a clinical relapse while the prednisone was tapered. Patient #2 spent 10 months in the hospital and currently continues to receive rituximab treatments when the CD19 count increases to 1%. On one occasion delay of treatment resulted in symptom recurrence. Patient #3 had 7 relapses in 5 years, most related with attempts to decrease the dose of steroids.

The main symptoms of this disorder including, agitation, myoclonus, tremor, and seizures, although not characteristic of a specific syndrome, are compatible with neuronal hyperexcitability, and consistent with the increased excitability noted in electrophysiological studies of DPPX-knock outs.[15] Interestingly, a truncation mutation of Kv4.2 identified in a patient with temporal lobe epilepsy resulted in aberrant excitability of cells expressing the mutant channel.[16] Altogether, these findings suggest that genetic or immunological alteration of the DPPX-Kv4.2 complex leads to neuronal hyperexcitability. In clinical practice, the combination of the neurological symptoms indicated above with severe diarrhea and non-organ specific antibodies (e.g. ANA) may lead to a wide differential diagnosis including among other Whipple's disease or lupus erythematosus, as occurred in our patients.

Figure 5:
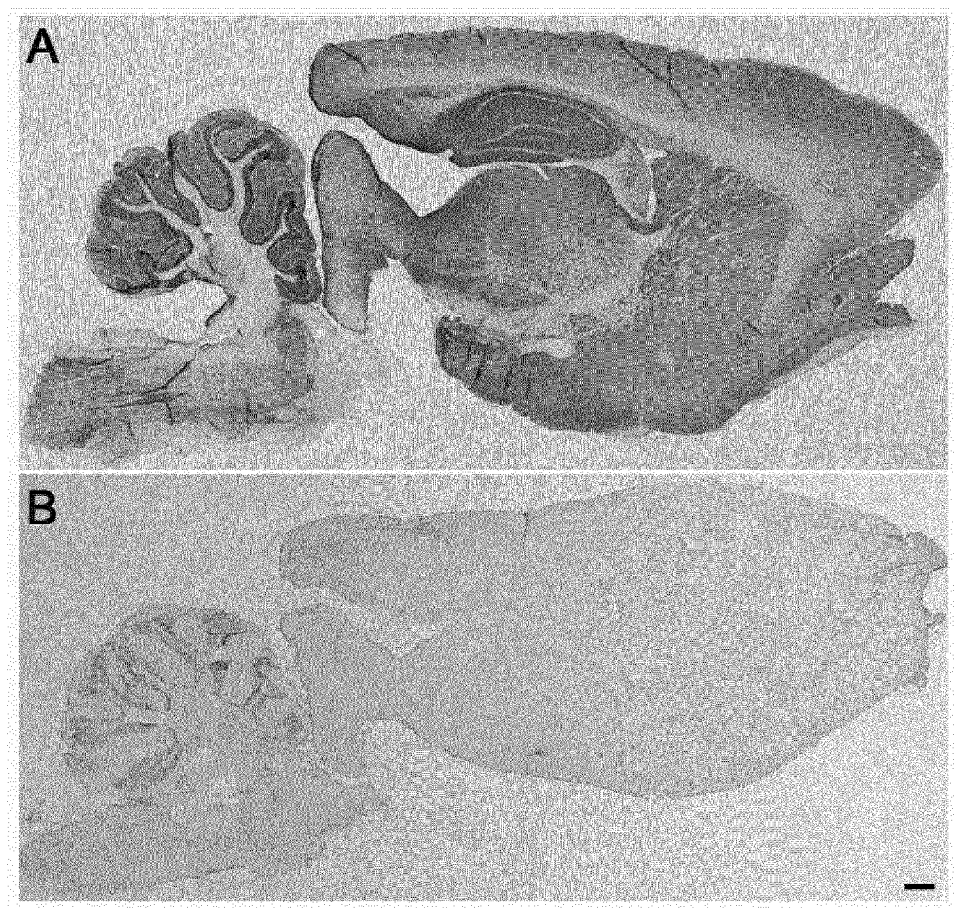
FIG. 5 shows a rat brain immunostaining with CSF of a patient.

At this time the significance of the diarrhea is unclear, but this symptom is notable because it was severe, lasted for several weeks, and only occurred at the initial episode of encephalitis. Moreover, review of our experience with encephalitis suspected to be autoimmune suggests a link between diarrhea and DPPX antibody-associated encephalitis. Indeed, among 1429 cases of encephalitis of unclear etiology examined between 2009 and 2012, only 11 had severe diarrhea at symptom onset. Three of these 11 patients correspond to the cases reported here, and the other 8 did not have DPPX antibodies; none of the 1418 cases without diarrhea had serum or CSF brain reactivity as that shown by DPPX antibody positive samples (see FIG. 5A). A plausible explanation for the association of diarrhea and DPPX antibody-associated encephalitis is that in some patients the immune response may result from molecular mimicry between DPPX and a yet unknown infectious agent. This paradigm would be similar to the mechanism that triggers GM1 autoantibodies in patients with Guillain-Barré syndrome and Campylobacter jejuni infection. Moreover, the robust expression of DPPX by neurons of the myenteric plexus support the possibility that patients' antibodies may alter the function of the plexus resulting in gastrointestinal hyperactivity, similar to the CNS hyperexcitability that occur when DPPX is ablated in brain.[15]

Against this background, the present invention provides a polypeptide or protein for use in diagnosis or treatment of an autoimmune disease in a subject, which polypeptide or protein is characterized in that it comprises one or more epitopes derived from the protein DPPX.

In some embodiments of the invention the polypeptide or protein according to the invention includes or has the amino acid sequence according to SEQ ID NO: 2, corresponding to the extracellular domain common to DPPX-S and DPPX-L from *rattus norvegicus*. Alternatively or in addition, the polypeptide or protein according to the invention may include or have the amino acid sequence according to SEQ ID NO: 3, corresponding to the intracellular and transmembrane domain of DPPX-L from *rattus norvegicus*. In other embodiments of the invention, the polypeptide or protein according to the invention, alternatively or in addition to the above, includes or has the amino acid sequence according to SEQ ID NO: 4, corresponding to the intracellular and transmembrane domain of DPPX-S from *rattus norvegicus*.

According to other embodiments of the invention, the polypeptide or protein for use according to the invention includes or has an amino acid sequence with at least 70, at least 75, at least 80, at least 90, at least 92, at least 94, at least 96, at least 98 or at least 99% sequence identity to the DPPX protein or the sequences according to SEQ ID NO: 1, SEQ ID NO: 2, SEQ ID NO: 3 or SEQ ID NO: 4. In other embodiments, the invention relates to a fragment of the DPPX protein or polypeptide having at least 20, 25, 30, 40, 50, 60, 70, 80, 90 or 100 consecutive amino acids of sequences according to SEQ ID NO: 1, SEQ ID NO: 2, SEQ ID NO: 3 or SEQ ID NO: 4. In further embodiments of the invention, the invention relates to a homolog of such fragments with at least 70, at least 75, at least 80, at least 90, at least 92, at least 94, at least 96, at least 98 or at least 99% sequence identity to the sequence of such fragments.

According to a preferred embodiment of the present invention, the polypeptide or protein comprises further amino acids, which are N-terminally or C-terminally attached and facilitate purification of the polypeptide or protein.

Such amino acids may, for example, constitute certain sequences or tags that are specifically recognized by other molecules, preferably proteins, more preferably antibodies. Such tags are extensively known in the art and comprise, for example, flag-tags, myc-tags or strep-tags.

According to another preferred embodiment, the polypeptide or protein for use according to the invention, alternatively or in addition to the above, it is linked to a reporter-molecule or a solid phase.

A reporter molecule, within the scope of the present invention, is understood to be a molecule that allows direct or indirect detection of either the absence or presence of the polypeptide or protein it is linked to, or the absence or presence of an antibody bound thereto. Many kinds of reporter molecules are known in the art, including for example radioactive labels, fluorescent dyes or proteins (e.g. fluorescine, tetramethylrodamine, green fluorescent protein (GFP)), haptenes (e.g. biotin) or enzymes (e.g. alpha-galactosidase A, luciferase, alkaline phosphatase or horseradish peroxidase, suitable for detection using enzyme convertible dyes). Such reporter molecules may be added to the target-protein either during protein synthesis (inclusion of radioactively labeled amino acids, generation of fusion proteins) or after protein synthesis by chemical coupling.

A solid phase in connection to the present invention relates to any solid substrate, to which a polypeptide or protein can be linked for example by direct or indirect covalent binding or by affinity binding via hydrogen bonds and/or lipophilic interaction. For example, the polypeptide or protein of the present invention may be linked to the material of a microtiter plate, the surface of magnetic beads, a membrane (e.g. a Nitrocellulose or PVDF membrane) or to the solid phase of a chromatography column or sheet.

The present invention also provides a nucleic acid and a vector encoding a polypeptide or protein according to the invention. In a preferred embodiment, the vector according to the present invention is adjusted for expression of the polypeptide or protein according to the invention.

Further, the present invention also provides a cell comprising a vector according to the invention. Such cell may be utilized by methods known in the art to produce copies of the vector or to express the polypeptide or protein according to the invention. Moreover, such cell also may constitute a diagnostic means for the detection of the binding of an antibody to the polypeptide or protein e.g. by presenting the polypeptide or protein on its surface.

The present invention also provides an in vitro diagnostic method characterized in that a sample from a subject is brought into contact with a polypeptide or protein according to the invention and the binding of an antibody from the sample to the polypeptide or protein is detected. According to a preferred embodiment of the present invention, the in vitro diagnostic method comprises detection of the binding of an antibody from the patient's sample to the polypeptide or protein with an immunofluorescence-test, protein microarray, ELISA, luminiscence-test, blot, radioimmune test, western blot or dot blot.

Such sample may be any isolated part of the human body, such as a part of tissue or body fluid, as long as the part contains antibodies. For example the sample is a liquid sample such as cerebrospinal fluid (liquor), blood or blood plasma, lymph or insterstitial fluid, or a tissue sample such as lymph node tissue, neural tissue, muscular tissue or tissue from the digestive tract.

Furthermore, a test kit for the detection of antibodies is provided in the context of the present invention, which test kit comprises one or more polypeptides or proteins according to the invention.

In addition, the present invention provides a pharmaceutical composition comprising a polypeptide or protein according to the invention. A pharmaceutical composition according to the invention may comprise one or more pharmaceutically active substances in addition to the polypeptide or protein according to the invention. In addition, a pharmaceutical composition according to the invention may comprise one or more pharmaceutical excipients. The pharmaceutical composition according to the invention is particularly useful for binding/absorbtion of antibodies of different classes (IgA, IgG) from a subject's blood or plasma and in particular for extracorporeal treatment of an autoimmune disorder. For example, said pharmaceutical composition may be employed in immunopheresis. In this connection, the present invention also provides a medical device coated with a polypeptide, a protein or a pharmaceutical composition according to the invention. For example, said medical device may be a device employed in conventional or immunopheresis and comprising surfaces coming into contact with blood or plasma of the subject to be treated.

Moreover, the present invention also provides a method for treating an autoimmune disease in a subject, the method comprising the steps of
  a. subjecting a liquid sample from a subject to an in vitro diagnostic method of the invention, and
  b. treating the subject with at least one suitable pharmaceutical substance and/or plasma exchange.

A suitable pharmaceutical substance, according to the invention may include a substance modulating, in particular suppressing, a subject's immune system or a specific part thereof. A suitable pharmaceutical substance may also be a substance for treatment of symptoms and conditions related to or caused by the autoimmune disorder to be treated. According to a preferred embodiment of the present invention, the suitable pharmaceutical substance is selected from the group consisting of Rituximab, prednisone, methylprednisolone, cyclophosphamide, lamotrigine, clonazepam, apiriprazole, phenytoin, mycophenolatemofetil, intravenous immunoglobulin, tacrolimus and cyclosporine.

In addition, the present invention provides a method for treating an autoimmune disease in a subject, wherein, preferably, the subject is a human, the method comprising the steps of a. taking blood or plasma from a subject,
  b. bringing the blood or plasma into contact with the pharmaceutical composition or the medical device of the invention in order to remove disease associated antibodies, and
  c. readministering the blood or plasma to the subject.

In such a method, e.g. immunopheresis, disease associated antibodies are removed from the subject's plasma by bringing the blood or plasma into contact with the immobilized polypeptide or protein according to the invention. Corresponding methods have been described e.g. for the treatment of a dilative cardiomyopathy based on the sequence of the beta-adrenergic receptor.[17]

LEGEND TO THE FIGURES

FIG. 1: Immunoprecipitation of DPPX

In cultures of dissociated rat hippocampal neurons, patients' antibodies showed intense reactivity with the neuronal cell surface (A), bar=10 µm. Immunoprecipitation of the antigen with serum of the index case is shown in B, where the precipitated proteins were run in a gel and subsequently stained with EZblue. Note that patient's antibodies precipitated a protein (band close to 102 kDa in lane P), which was excised from the gel and analyzed by mass spectrometry, demonstrating sequences of DPPX. Lane N is the precipitate obtained from control serum. Immunoblot of these proteins with a rabbit polyclonal antibody against DPPX (1:1000, developed by BR) confirmed that the band corresponded to DPPX (C).

FIG. 2: Expression of DPPX in Myenteric Plexus

Figure 2A:
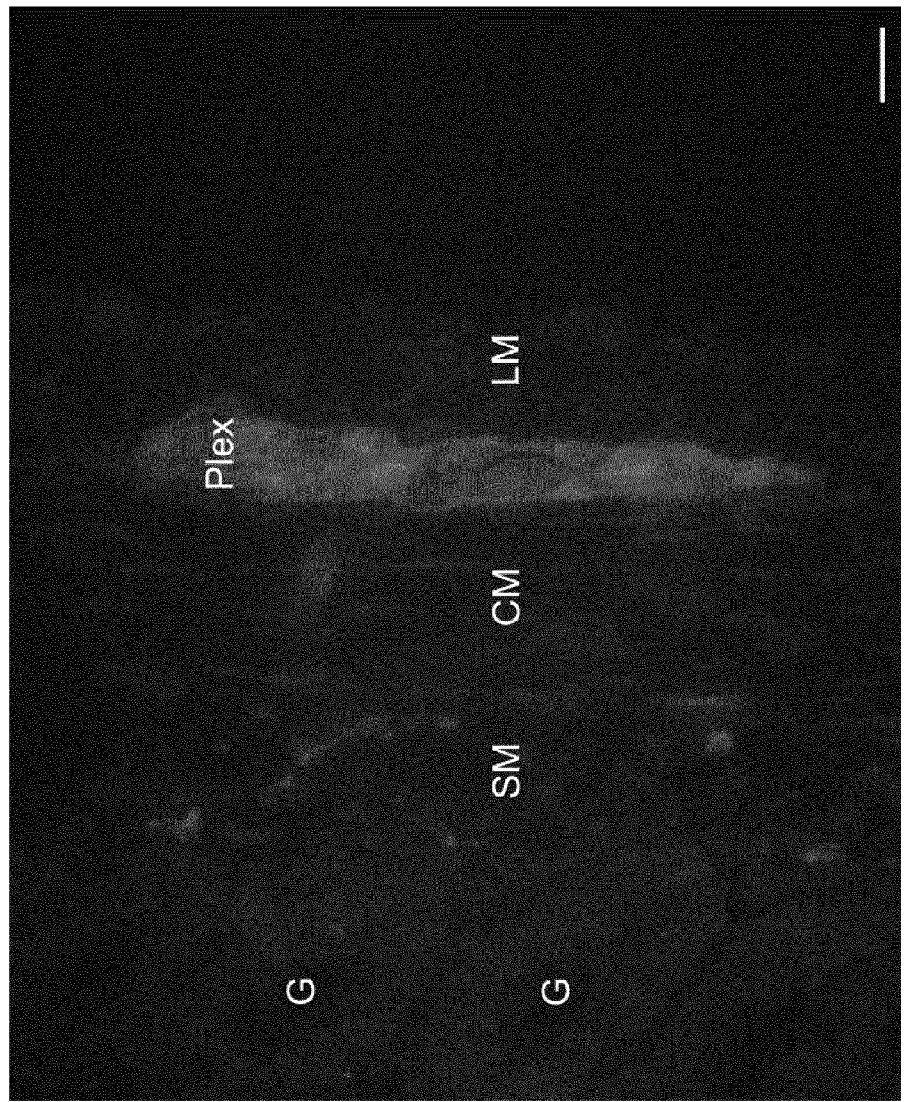
FIG. 2 shows the expression of DPPX in the myenteric plexus.

Transverse section of small bowel of rat showing the longitudinal muscular layer (LM), circular muscular layer (CM), submucosal layer (SM), and glans (G). The myenteric plexus (Plex) is revealed as clusters of large neurons between the two muscular layers. (FIG. 2A)

Figure 2B:
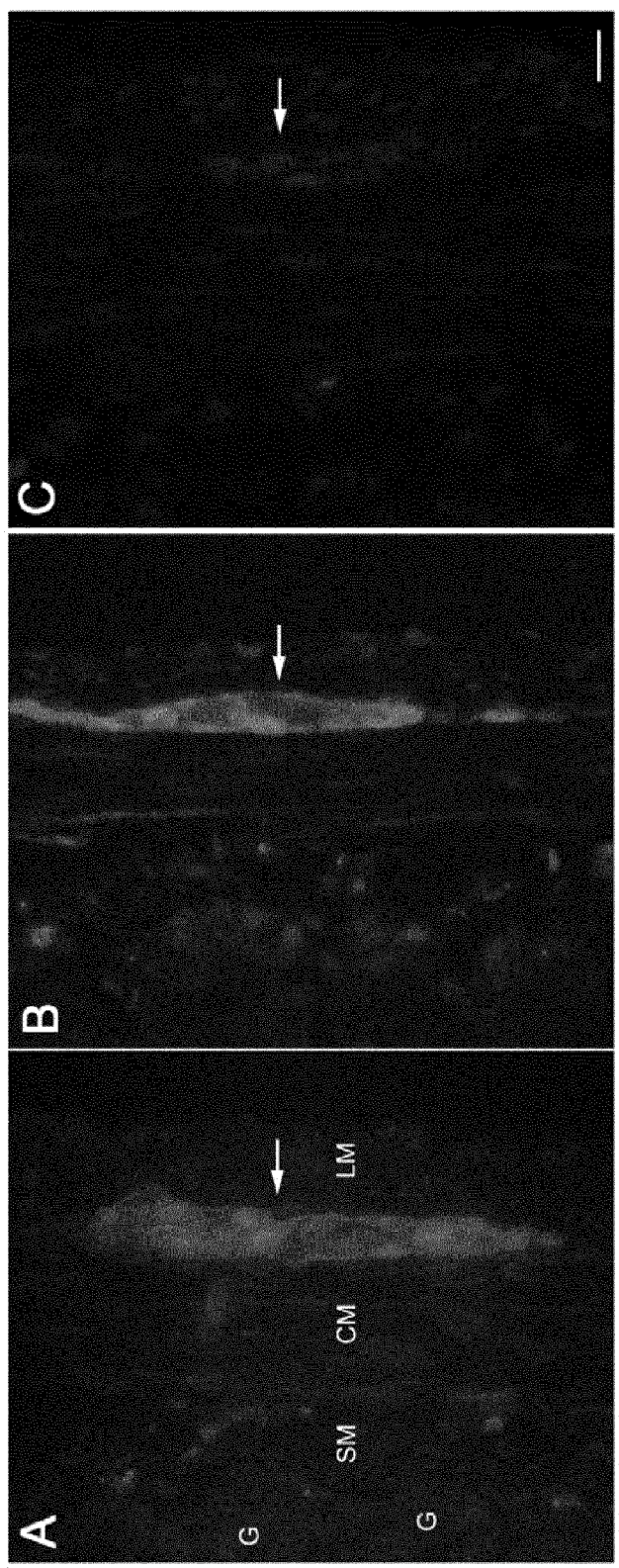

In the 3 panels (A-C) the nuclei of the neurons (red) was labeled with anti-Hu (a highly specific neuronal marker). Panel A, shows in green the DPPX immunostaining using a rabbit polyclonal antibody (1:1000, developed by BD); panel B shows the DPPX reactivity of serum from one of the patients with encephalitis, and panel C shows the lack of reactivity of serum from a healthy subject. Note that DPPX is predominantly expressed in the cytoplasm-membrane of the large clustered neurons of the myenteric plexus, and is also detected in a fine longitudinal pattern in CM and SM where the submucosal plexus is located. Bar=20 µm. (FIG. 2B)

Figure 3:
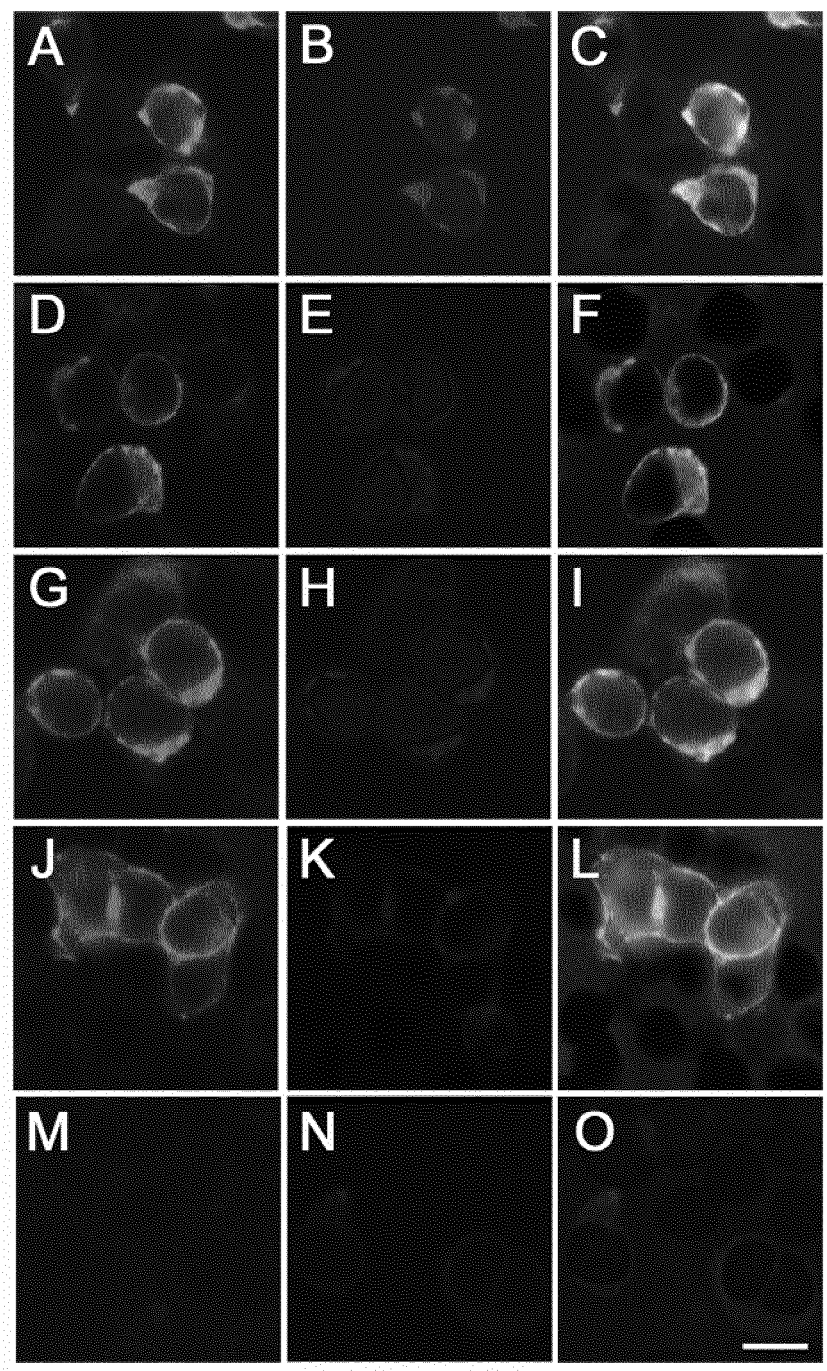
FIG. 3 shows the analysis of DPPX antibodies using a cell-based assay.

FIG. 3: Analysis of DPPX Antibodies Using a Cell-Based Assay

HEK 293 cells expressing DPPX-L (see below in example 4) immunostained with patients' serum (A, D, G, J) and a mouse monoclonal antibody against DPPX (B, E, H, K). The merged reactivities are shown in the corresponding panels (C, F, I, L). Similar studies comparing the serum of a healthy individual and the DPPX monoclonal antibody are shown in M and N, and the merged reactivities in O. Note that patient's antibodies immunoreact with cells expressing DPPX. Bar=10 µm.

Figure 4:
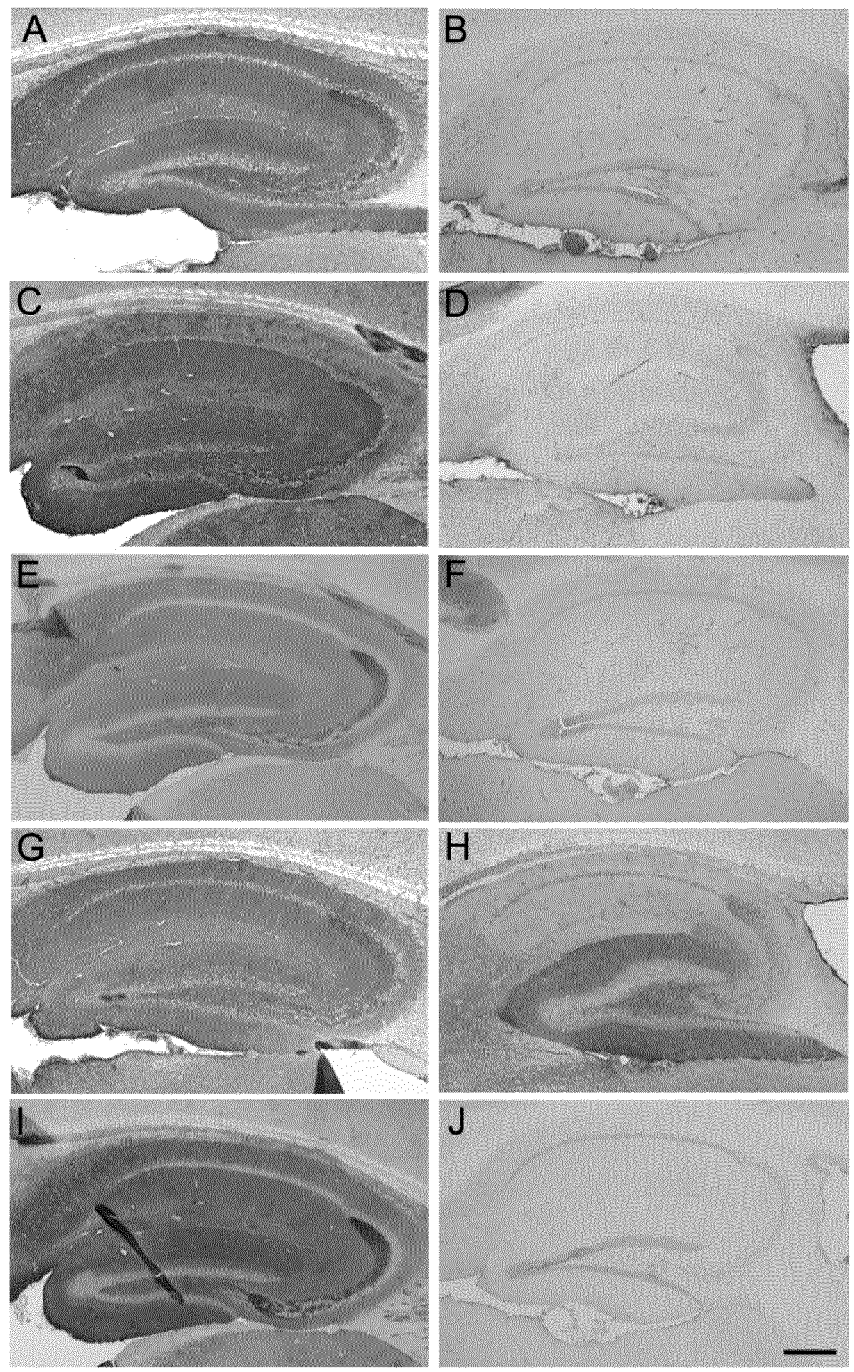
FIG. 4 shows a comparison of patient's serum reactivity using brain of DPPX-null mutant and wild type mice.

FIG. 4: Comparison of Patients' Serum Reactivity Using Brain From DPPX-Null Mutants and Wild Type Mice The reactivity of patients' serum with the hippocampus of wild type mice is shown in A, C, E and G. The reactivity of a rabbit polyclonal DPPX antibody with the hippocampus of wild-type mice is shown in I. Panels on the right side show the results of a similar experiment but using the hippocampus of DPPX-null mice. Note that the reactivities of the sera of the first three patients (cases 1, 2, and 3 of Table 1) and the rabbit polyclonal DPPX antibody are abrogated in the hippocampus of DPPX-null mice (panels B, D, F, J). Patient 4, not included in the table (panels G and H) showed remaining reactivity with the hippocampus of DPPX-null mice indicating that this patient had two antibodies, one against DPPX and the other against an unknown antigen. Bar=200 μm.

FIG. 4: Rat Brain Immunostaining with CSF of a Patient

Sagittal sections of rat brain immunostained with CSF of a patient (A) and a healthy individual (B). Note that the patient's CSF shows intense reactivity with the neuropil of brain, predominantly the hippocampus and cerebellum, while control CSF produces no reactivity. Bar=500 μm.

Figure 6:
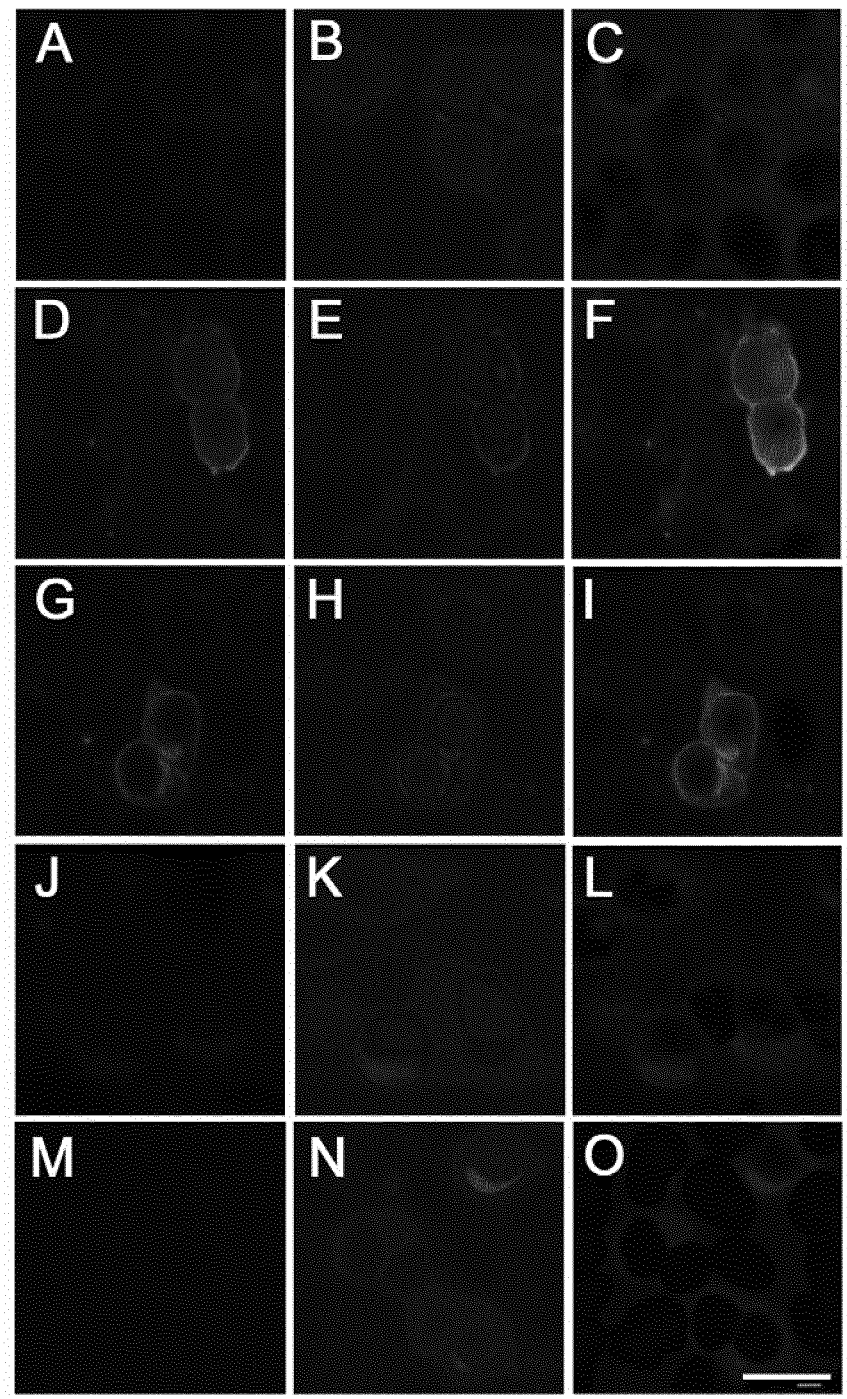
FIG. 6 shows an analysis of patient's antibodies using a cell-based assay expressing a mutant (DPPXed-myc) with the extracellular domain of DPPX deleted.

FIG. 6: Analysis of Patients' Antibodies Using a Cell-Based Assay Expressing a Mutant (DPPXed-myc) with the Extracellular Domain of DPPX Deleted HEK 293 cells expressing the mutated DPPXed-myc construct immunostained with patients' serum (A, D, G, J) and a mouse monoclonal Myc-tag antibody diluted 1:500 (B, E, H, K). The merged reactivities are shown in the corresponding panels (C, F, I, L). Similar studies using the serum of a healthy individual and the anti-Myc-tag antibody are shown in M and N, and the merged images in O. Note that two patients (panels A and J) had antibodies that did not react with this construct indicating that the target epitopes were present only in the extracellular domain (FIG. 3); in contrast, two patients had antibodies that reacted with this construct indicating that they recognized intracellular epitopes (D and G) in addition to extracellular epitopes present in the DPPX full construct (FIG. 3) and in cultures of live neurons. Bar=10 μm.

Figure 7:
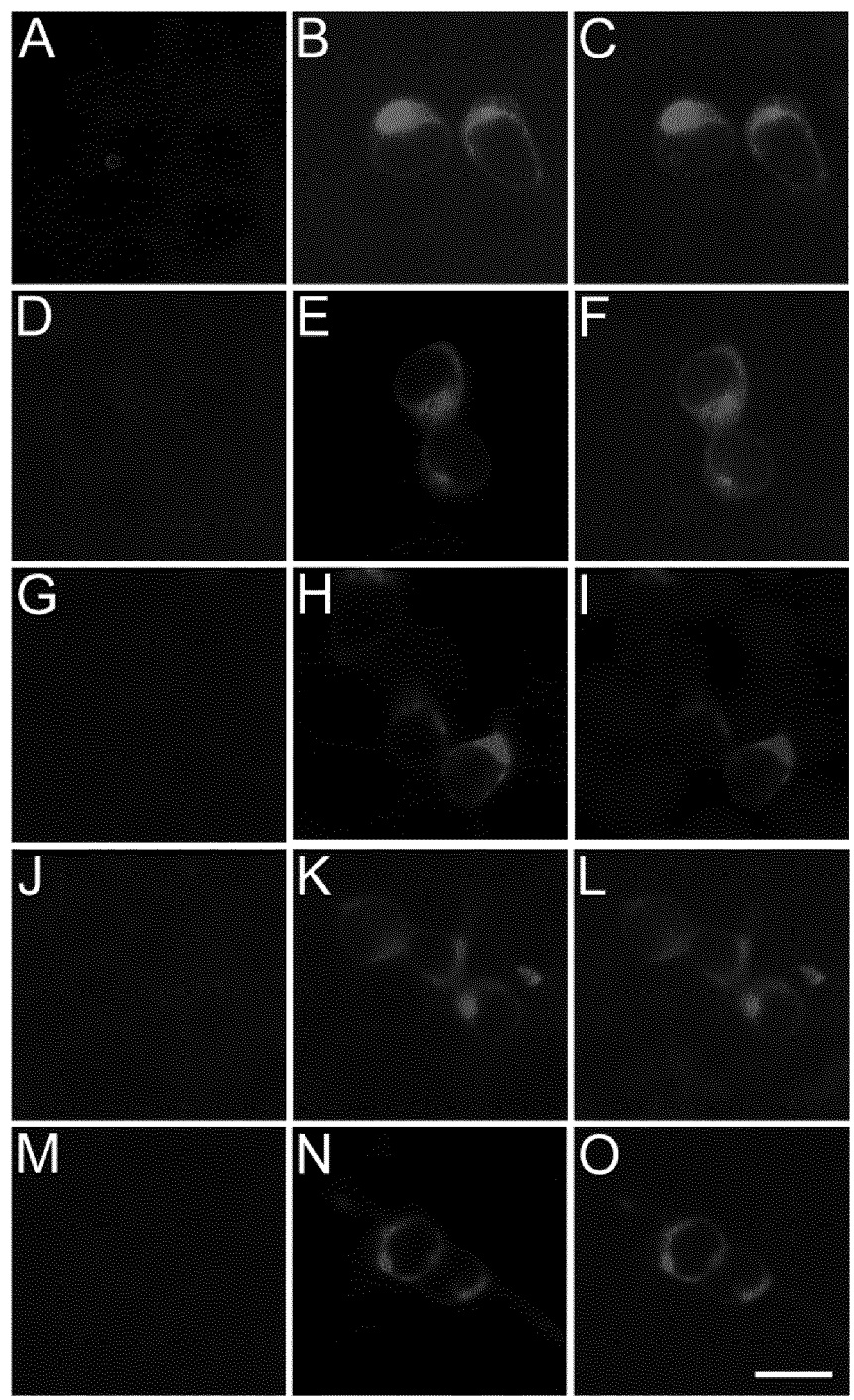
FIG. 7 shows the analysis of patient's antibodies using a cell-based assay expressing Kv4.2

FIG. 7: Analysis of Patients' Antibodies Using a Cell-Based Assay Expressing Kv4.2

HEK 293 cells expressing Kv4.2 immunostained with patients' serum (A, D, G, J) and a rabbit polyclonal antibody (Alomone labs, #APC-023) against Kv4.2 (B, E, H, K). The merged reactivities are shown in the corresponding panels (C, F, I, L). Similar studies comparing the serum of a healthy individual and the rabbit polyclonal antibody are shown in M and N, and the merged images in O. Note that patient's antibodies do not recognize Kv4.2. Bar=10 μm.

EXAMPLES

Report herein are the clinical and immunological features of 4 patients with prominent neuropsychiatric symptoms (preceded in 3 by intense diarrhea) and antibodies against a novel cell surface antigen, dipeptidyl-peptidase-like protein-6 (DPP6 or DPPX), a cell surface auxiliary subunit of the Kv4.2 potassium channels. In addition to the known robust expression of DPPX in the hippocampus and cerebellum, the inventors show that DPPX is also expressed in the myenteric plexus.

The observation of 4 patients with subacute onset of neuropsychiatric symptoms and serum or CSF antibodies showing a similar pattern of immunostaining of the neuropil of rodent hippocampus and cerebellum, as well as immunolabeling of the cell-surface of dissociated cultured hippocampal neurons led to immunoprecipitate the target antigen. Serum or CSF of 149 subjects including patients with autoimmune inflammatory and non-inflammatory encephalopathies, and normal individuals served as controls.

Example 1

Patients

Patients are described in detail below (cases 1 to 3), and summarized in Table 1. The fourth case was a 76 year-old man who developed prominent diarrhea and weight loss along with rapidly progressive confusion, cognitive decline, seizures, unsteady gait, and evidence of intrathecallgG production (IgG index 1.49); he is not included in the table due to limited information and lack of follow-up.

Patient 1:

A 61 year-old man with history of obesity, hypertension, and adult-onset diabetes mellitus was admitted for four weeks of abdominal pain and diarrhea followed by subacute change in mental status, characterized by depression, aggression, withdrawal, visual hallucinations, mutism, myoclonus and an exaggerated startle response. MRI of the abdomen showed a fatty liver but no evidence of tumor, and extensive GI workup was negative for fecal leukocytes, clostridium difficile, parasites and ova. Endoscopic biopsies from stomach, small bowel, and colon showed only chronic gastritis (serum *H. Pylori* IgG positive without bacterium on histology). The diarrhea persisted for over one month without other symptoms of autonomic dysfunction.

CSF, MRI and EEG studies are described in Table 1. CSF PCR for HSV, VZV, Tropherymawhippelii, and enterovirus were negative. Rheumatologic, paraneoplastic, and neuronal cell surface antibody panels (which also included the glycine receptor) were negative. Whole body CT and PET scans and testicular ultrasound did not reveal a cancer.

The patient was briefly intubated for worsening mental status, and treated with intravenous methylprednisolone (1000 mg/day×5 days) with notable neurologic improvement. He was then placed on a prolonged oral steroid taper over 4 months and discharged to a skilled nursing facility. Four months later he was readmitted with worsening mental status and a urinary tract infection. Treatment with antibiotics followed by IVIg (2 grams/kg over 5 days) resulted in brief neurologic improvement. He subsequently developed sepsis and was transferred to the ICU requiring a tracheotomy and PEG tube. Repeated IVIg did not improve his mental status. He was then treated with Rituximab (1000 mg iv×2 doses 15 days apart) and the prednisone was titrated to 5 mg every other day. The clinical course was complicated by urinary tract infections and pneumonia, and his mental status remained poor for 5 more months. At his best he could mouth a few words and follow simple commands. One striking finding on the exam at this stage of disease was an exaggerated startle response to sound and touch. In addition, he exhibited frequent episodic myoclonus, oral dyskinesias and paratonia; the muscle strength was normal.

He was eventually treated with plasma exchange. After the first exchange, he was able to converse readily with his examiners and answer questions, but not enough to participate in formal cognitive testing. Subsequently, he received monthly intravenous pulses of cyclophosphamide with a steady but incomplete improvement in cognition. He was able to return home 15 months after symptom onset. On follow-up 21 months after symptom onset, and after having received 9 monthly doses of intravenous cyclophosphamide, he was still at home with family, but required assistance with many activities of daily living. On cognitive testing, orientation was relatively preserved but there were impairments in attention and concentration, executive functioning, abstraction, visual-spatial functioning and phonemic fluency. Testing of verbal memory revealed successful encoding (cueing required). He scored 9 out of 30 points on the Montreal Cognitive Assessment (MOCA). He has lost 45 kg during the course of the disease.

Patient 2:

In April 2008, a 45 year-old woman presented with progressive diarrhea and weight loss of 30 kg. Endoscopy and biopsy failed to demonstrate a cause. Over the ensuing 6 to 8 weeks she noted that she was becoming cognitively impaired, making an increasing number of errors at work. In July, she was admitted to the hospital for agitation and hallucinations. At examination, she was found to have paranoia, anxiety, insomnia, and complained of night sweats. These symptoms coupled with the identification of serum antinuclear antibodies (ANA>2560) initially led to the diagnosis of lupus erythematosus.

In September, the patient was transferred to a Neurology unit. On arrival she was found to have occasional myoclonic jerks, resting tremor in all limbs, marked bilateral horizontal nystagmus, and generalized hyperreflexia with downgoing toes. Brain MRI was normal, and EEG showed intermittent episodes of generalized slow-wave theta and delta activity. Extensive blood tests for infection and autoimmune disorders were negative except for the previously noted ANA (homogenous pattern). CSF analysis revealed 15 white blood cells (predominantly lymphocytes), normal protein and glucose concentration, and unmatched oligoclonal bands. CT of the chest, abdomen and pelvis suggested adnexal thickening that was confirmed on ultrasound. An FDG-PET scan was normal. Over the following 3 weeks, she became increasingly agitated with worsening myoclonus and course resting tremor in all limbs. Diazepam provided some symptomatic relief, but over the following 2 weeks she developed episodes of reduced level of consciousness and orofacial movements. Repeat EEG demonstrated low voltage generalized epileptiform discharges, and anti-epileptic medication was started. Repeat brain MRI brain was normal. On the basis of a presumed inflammatory encephalopathy, she received intravenous methylprednisolone (1 g daily for 3 days) without effect. The seizure frequency worsened, and she developed frequent episodes of status epilepticus that were refractory to numerous antiepileptic medications, ultimately necessitating sedation, intubation, and ventilatory support. Any attempt to wean the sedation resulted in recurrence of status epilepticus. On the basis of the adnexal lesion, she underwent hysterectomy and bilateral salpingo-oophorectomy. The pathology demonstrated a fibroid uterus. She was then started on intravenous immunoglobulin (IVIg) resulting in slow and progressive improvement, allowing extubation and discharge from the ICU.

In January 2009, serum and CSF analysis revealed a novel autoantibody reacting with the cell surface of neurons. This finding and the persistence of neurological symptoms led to the initiation of treatment with Rituximab that was associated with a faster recovery, and she was discharged home in May 2009. Afterwards, she continued to improve and the antiepileptic medication was discontinued. Currently, she has normal cognition and lives independently. She undergoes regular surveillance of her CD 19 lymphocyte count and receives further treatment with Rituximab when the count raises to 1%. On one occasion this treatment was delayed, resulting in recurrent tremor and nystagmus.

Patient 3:

In June 2006, this 58 year old right handed woman developed hallucinations and unsteadiness, and was admitted to the hospital. The following tests were normal: blood cell count and chemistry, thyroid function tests, ANA and ds DNA antibodies, and studies for Lyme disease, Rocky Mountain spotted fever, Coxsackie, Babesia, and hepatitis C virus. ESR was slightly elevated at 43. Brain MRI showed nonspecific white matter changes without contrast enhancement. Chest x-ray was normal. Carotid ultrasound showed no significant stenosis. EEG revealed mild slowing. CSF analysis showed 11 WBC/mm3, all mononuclear, protein of 50 mg/dl, and glucose of 74 mg/dl. CSF HSV PCR, viral cultures, Lyme titer, cryptococcal antigen were all negative. There was one oligoclonal band. She was seen by consultants from Neurology, Infectious Disease, Internal Medicine, and Psychiatry, and treated with risperidone, gabapentin, escitalopram, and carvedilol. With these medications she returned to about 80% of her usual self and was discharged home.

By November 2006, she developed increased unsteadiness, with frequent falls, tremors, dysarthria, recurrent hallucinations, and sleep walking, and was readmitted. Repeat brain MRI, MR angiography, and cerebral angiogram were normal. Abdominal MRI showed a benign appearing adrenal adenoma. EEG showed background slowing predominantly over the right hemisphere. CT scan of the chest, abdomen and pelvis showed some fluid around a shoulder, a homogenously enhancing pancreas, and the indicated adrenal lesion. Temporal artery biopsy was negative. CSF showed 1 white blood cell, 0 red blood cells, glucose of 87 mg/dl, protein of 38 mg/dl, and negative cultures. Studies for HSV, cryptococcal antigen, West Nile virus, angiotensin converting enzyme (ACE), and cytology were all negative. Anti-single stranded DNA was positive, but anti-double stranded DNA was negative once and positive once at 62 (nl: <25). Negative or normal tests included rheumatoid factor, anti-cardiolipin antibody, IgG, SPEP, B12, SSA, SSB, Lyme, HSV, lead, histone antibody, LA, ANA, ANCA, hepatitis B surface antigen, ceruloplasmin C3, C4, RNP, Smith, RPR, CRP, B12, RF, cryoglobulins, urine mercury and arsenic, blood arsenic, and a comprehensive paraneoplastic panel. She was treated with prednisone 60 mg daily and improved.

Over the next 2 months the prednisone was tapered to 10 mg daily and she was evaluated at our institution for the first time in February 2007. Past history was remarkable for hypertension, cholecystectomy, and hip replacement. Medications included prednisone 10 mg daily, pantoprazole, amlodipine, isosorbidemononitrate, carvedilol, clonidine, alendronate, levofloxacin and albuterol. On examination she was alert and attentive with normal language, recalled 2/3 words and 3/3 with prompts. She had congenital nystagmus, but the cranial nerves were otherwise normal. She showed dorsiflexion weakness of the ankles. Sensation and reflexes were normal. Gait was slow with poor tandem. Repeat rheumatological and paraneoplastic panels, porphyrins, beta-2-glycoprotein, cryoglobulins, and TPO antibodies were all negative.

Prednisone was tapered off over the next month and she worsened with hallucinations, decreased speech, tremors, myoclonus, and ataxia, and was admitted to the hospital. Brain MRI showed a non-acute but new right frontal infarct. Brain SPECT showed moderate global hypoperfusion. EEG showed mild background slowing. Repeat CSF analysis was normal. Trans-esophageal echocardiogram showed a small atrial septal defect. Repeat cerebral angiogram showed only mild atherosclerotic changes at the carotid bifurcations. Brain biopsy revealed an infarction with no evidence of inflammation or vasculitis. Repeat CT of chest, abdomen, and pelvis showed the previously noted adrenal adenoma and renal cysts. She was treated with intravenous steroids, followed by oral steroids, aspirin, atorvastatin, and sertraline. Her neurological symptoms improved and she was discharged on prednisone 80 mg daily. Subsequently, the prednisone was slowly tapered and lamotrigine, clonazepam, and aripiprazole were added. Although the symptoms improved she continued with waxing and waning dysarthria, unsteadiness, tremors, and myoclonus. CSF analysis in December 2007 showed 1 WBC, glucose of 83 mg/dl, protein of 53 mg/dl, and positive oligoclonal bands. Mycophenolatemofetil 100 mg twice daily was added.

By April 2008 the dose of prednisone was further decreased. She then developed shingles and her symptoms worsened, with altered mental status and ataxia, and she was readmitted. CSF analysis showed 53 WBC (94% lymphocytes and 6% mononuclear), glucose of 70 mg/dl, and protein of 62 mg/dl. PCR for HSV, HHV-6, VZV, CMV, EBV, EEE, SLE, enterovirus, and West Nile virus were all negative. She was treated with IV acyclovir, the prednisone dose was increased, and the mycophenolate discontinued. By that time, CSF analysis revealed a novel autoantibody against the cell surface of neurons. Intravenous immunoglobulin (IVIg) 2 g/kg was started and she was discharged on prednisone 80 mg daily with slow taper and monthly cycles of IVIg.

In September 2008, after the prednisone was reduced to 50 mg daily, she developed increased hallucinations. The IVIg was stopped, and the steroid dose was increased, first using iv steroids and subsequently oral steroids. Rituximab was started (650 mg weekly×4 doses). Repeat CSF testing showed absent reactivity with the cell surface of neurons. She improved but again deteriorated during a slow steroid taper from 80 mg daily to 50 mg daily. In November 2008 she received 1 dose of 1000 mg of IV cyclophosphamide, but developed cryptococcal pneumonia precluding further treatment. Neuropsychological testing showed impairments in visual motor speed, comprehension of multistep commands, and manual sequencing. Less impaired, but below expectation, were some memory performances, auditory attention, visual analysis, and trial-and-error reasoning. Other performances in language comprehension/expression, judgment, memory for stories and orientation were consistent with the estimated premorbid function. Because of worsening confusion she was treated with 5 courses of plasma exchange and continued daily prednisone. Repeat neuropsychological testing in January 2009 showed generally stable cognition compared to November 2008. Continuous EEG showed background slowing but because of waxing and waning mental status phenytoin was also added. She improved and was discharged to rehabilitation on prednisone 50 mg daily and phenytoin 100 mg twice daily.

She was readmitted in February 2009 with bilateral deep venous thrombosis and pulmonary emboli and treated with anticoagulation and inferior vena cava filter placement. She was discharged in March 2009 on prednisone 45 mg daily, phenytoin 100 mg twice daily along with medications for her other medical conditions. The prednisone was gradually tapered over the next 30 months and eventually discontinued. As of January 2012, 4 months after stopping prednisone, she had no worsening symptoms and was alert, attentive, fully oriented, with 3/3 recall, and good knowledge of current events. She has no tremors, myoclonus, or hallucinations. She walks with a slightly wide base and has poor tandem gait.

Results:

All 4 patients (2 male, 2 female; age range 45-76 years) developed a rapidly progressive encephalopathy characterized by agitation, delusions, hallucinations, and myoclonic jerks, which in 3 patients associated with prominent diarrhea of unclear etiology. All had confirmed or clinically suspected seizures and CSF pleocytosis with evidence of intrathecal production of IgG or oligoclonal bands. Detailed information from 3 patients showed that after multiple immunotherapies all had substantial recovery at the last follow-up (18-68 months from symptom onset); minimal follow-up information was available for the fourth patient.

Example 2

Immunohistochemistry on Rat Brain, Small Bowel, and Neuronal Cultures

Immunohistochemistry of Rat Brain and Myenteric Plexus:

Female Wistar rats were euthanized and the brain and small bowel removed, sectioned (brain sagittally, bowel transversally), immersed in 4% paraformaldehyde at 4° C. for 1 hour, cryoprotected with 40% sucrose for 24 hours, and snap frozen in isopentane chilled in liquid nitrogen.[18] Seven-micrometer-thick tissue sections were then sequentially incubated with 0.3% $H_2O_2$ for 20 minutes, 10% goat serum for 1 hour, and patient or control serum (1:200), CSF (1:2), or a polyclonal rabbit antibody to DPPX (diluted 1:1000, antibody developed by BR) at 4° C. overnight. After using the appropriate secondary biotinylated antibodies (goat anti-human BA-3000, or goat anti-rabbit BA-1000, Vector laboratories, all 1:2,000), the reactivity was developed with the avidin-biotin-peroxidase method, as reported.[18]

For analysis of expression of DPPX in small bowel of rat, a biotinylated human anti-Hu IgG (a specific neuronal nuclear marker) was used at 1:200 dilution along with the above indicated polyclonal rabbit DPPX antibody (1:1000) or the CSF of patients with DPPX antibodies, followed by avidin-rhodamine (1:500) and the appropriate secondary fluorescent antibodies at 1:1000 (goat anti-rabbit IgGAlexa Fluor 488, or goat anti-human IgGAlexa Fluor 488; Molecular Probes, Invitrogen). Results were photographed under a fluorescence microscope using Zeiss Axiovision software (Zeiss, Thornwood, N.Y.).

Immunocytochemistry on Neuronal Cultures:

Rat hippocampal neuronal cultures were prepared as reported.[19] Live neurons grown on coverslips were incubated for 1 hour at 37° C. with patient or control serum (final dilution 1:750) or CSF (1:10). After removing the media and extensive washing with phosphate-buffered saline (PBS), neurons were fixed with 4% paraformaldehyde, permeabilized with 0.1% Triton X-100, and immunolabeled with goat anti-human IgGAlexa Fluor 488 (1:1000).

Results:

All 4 patients had antibodies in serum or CSF that reacted with the neuropil of brain of rodents (supplementary FIG. 1) and the cell surface of live, non-permeabilized cultures of dissociated rat hippocampal neurons (FIG. 1A).

Immunohistochemical analysis of small bowel demonstrated that DPPX was specifically expressed by neurons of the myenteric plexus and that patients' antibodies also reacted with DPPX expressed in these neurons (FIG. 2).

Example 3

Immunoprecipitation, Mass Spectrometry, and Immunoblot

Immunoprecipitation and Immunoblot:

Cultures of rat hippocampal neurons were grown in 100 mm wells (density $10^6$ neurons/well), and incubated at 37° C. with filtered patient serum (diluted 1:100) for 1 hour. Neurons were then washed with PBS, lysed with buffer (NaCl 150 mM, EDTA 1 mM, tris(hydroxymethyl)aminomethane [Tris]-HCl 100 mM, deoxycholate acid 0.5%, 1% Triton X-100 [Sigma Labs, St. Louis, Mo.], pH 7.5) containing protease inhibitors (P8340; Sigma Labs), and centrifuged at $16.1 \times 10^3$ g for 20 minutes at 4° C. The supernatant was retained and incubated with protein A/G agarose beads (20423; Pierce, Rockford, Ill.) overnight at 4° C., centrifuged, and the pellet containing the beads with patients' antibodies bound to the target cell surface antigen was then washed with PBS, aliquoted, and kept at −80° C. An aliquot of this pellet was resuspended in Laemmli buffer, boiled for 10 minutes, separated in a 4 to 15% sodium dodecyl sulfate polyacrylamide gel electrophoresis, and the proteins visualized with EZBlue gel staining (G1041; Sigma Labs). Visible protein bands precipitated by patient's serum were excised from the gel and analyzed using mass spectrometry at the Proteomics Core Facility of the Genomics Institute at the Abramson Cancer Center (University of Pennsylvania). After characterization of the antigen, frozen aliquots of the indicated pellets were separated in a sodium dodecyl sulfate polyacrylamide gel electrophoresis as described earlier, transferred to immobilon-P membrane (Millipore IPVH00010) and blotted with the indicated antibody against DPPX (developed by BR, 1:0000). The reactivity was developed using the appropriate biotinylated secondary antibodies (1:2000) and the avidin-biotin peroxidase and diaminobenzidine method.

Mass Spectrometry:

Protein bands from the gels were cut and sent for mass spectrometry to the Proteomics Facility at the University of Pennsylvania. Protein bands were trypsin digested and analyzed with a nano liquid chromatography (nano LC)/nano spray/linear ion trap (LTQ) mass spectrometer (Thermo Electron Corporation, San Jose, Calif.) as reported.[20] Briefly, 3 µl trypsin digested sample was injected with autosampler from Eksigent (Dublin, Calif.). The digested samples were separated on a 10 cm C18 column, using nano LC from Eksigent with 200 µl/minute flow rate, 45 minute gradient. Online nanospray was used to spray the separated peptides into LTQ, and Xcalibur software (Thermo Scientific, Waltham, Mass.) was utilized to acquire the raw data. The raw data files were searched using Mascot (Matrix Science, Boston, Mass.) against the NCBI and Swissprot databases (Swiss Institute of Bioinformatics (Basel, Switzerland). The cutoff for confident protein identification was ≥70.

Results:

Immunoprecipitation of the target antigen with serum of one of the patients, followed by electrophoretic protein separation and EZBlue gel staining showed a distinct band of approximately 100 kDa that was not present in the immunoprecipitate using a control serum (FIG. 1B). Excision of the band from the gel and analysis by mass spectrometry demonstrated that it contained sequences derived from DPPX (scores 6441, 5945, and 383; cutoff score for a confident protein identification ≥70). This finding was confirmed by immunoblotting of the precipitate with an antibody specific for DPPX (FIG. 1C).

Example 4

Immunocytochemistry on HEK293 Cells

HEK293 cells were transfected with plasmids containing rat DPPX-S (short cytoplasmic domain of 32 amino acids), DPPX-L (long cytoplasmic domain of 88 amino acids), DPPXed-myc (DPPX construct with extracellular domain deleted, and linked to a myc-tag), rat Kv4.2, human DPPX (DPP6; Origene, sequence NM_001039350.1; SEQ ID NO: 1), human DPP10), or plasmid without insert (control).[11] In other experiments, cells were co-transfected with DPPX and Kv4.2 in equimolar ratios. The reactivity of patients' antibodies was then assessed as previously reported.[21] For this purpose, cells were grown for 24 hours after transfection before assessment. Transfected cells were fixed in 4% paraformaldehyde, permeabilized with 0.1% Triton X-100 and then incubated with patients' serum (1:200) or CSF (1:2) and depending on the antigen of interest one of the following antibodies, DPPX (rabbit polyclonal developed by BR diluted 1:1000; rabbit polyclonal antibody abcam 41811 diluted 1:200 or mouse monoclonal Sta Cruz #365147 diluted 1:500), Kv4.2 (rabbit polyclonal, Alomone labs, #APC-023 diluted 1:500), or a myc-tag antibody (mouse monoclonal myc-tag 9B11, Cell Signaling, diluted 1:2000) for 2 hours, and the corresponding fluorescent secondary antibodies ((goat anti-human IgG Alexa Fluor 488; goat anti-rabbit IgGAlexa Fluor 555, or goat anti-mouse IgGAlexa Fluor 555, all used at 1:1000). Results were photographed under a fluorescence microscope using Zeiss Axiovision software (Zeiss, Thornwood, N.Y.).

Results:

HEK293 cells transfected with rat DPPX-S or DPPX-L showed similar reactivity with patients' serum or CSF, consistent with the recognition of an extracellular epitope (FIG. 3 shows the reactivity with DPPX-L; similar reactivity was obtained with DPPX-S, not shown). Patients' antibodies did not react with cells expressing Kv4.2 (supplementary FIG. 2), and the reactivity with DPPX was not modified when it was co-expressed with Kv4.2 (data not shown). Further analysis using a rat DPPX plasmid in which the extracellular domain was deleted (DPPXed-myc)[11] showed abrogation of reactivity with serum and CSF of patients 1 and 4, and weak reactivity with serum and CSF of patients 2 and 3, indicating that the latter two patients had antibodies against cell surface and intracellular epitopes (panels D and G of supplementary FIG. 3). In addition, HEK293 cells transfected with human DPPX also showed reactivity with serum or CSF of the 4 patients with DPPX antibodies (shown to react with rat sequences of DPPX) while they did not show reactivity with serum and CSF from 10 healthy individuals. Although DPPX and DPP10 have 51% amino acid sequence identity,[12] patients' antibodies did not react with DPP10 (data not shown). Overall, these findings demonstrate that patients' antibodies specifically target DPPX, but not the Kv4.2 channel, and that some patients have antibodies against both, the extracellular and intracellular domains of DPPX.

The inventors next determined in a cell-based assay co-expressing DPPX and Kv4.2 the reactivity of serum or CSF of the 149 controls. None of these subjects was found to have antibodies reacting against these 2 proteins, suggesting that antibodies against DPPX are specific to a subgroup of patients with autoimmune encephalitis. In contrast, a patient without encephalitis who had a thymoma and seronegative myasthenia gravis (included in the controls) had antibodies to DPP10, but not DPPX (Martinez-Hernandez, data not shown).

Example 5

Immunohistochemistry with Wild Type and DPPX-Null Mice

Wild-type and DPPX-null mice were generated and genotyped as previously reported.[22] The brains were removed, sagittally sectioned, processed, and examined by standard avidin-biotin-peroxidase immunohistochemistry using patients' serum (1:200) or CSF (1:5) as indicated for rat brain.

Results:

To further confirm the specificity of patients' antibodies for DPPX, immunohistochemistry with brain of wild-type mice was compared with that of DPPX-null mice. These experiments demonstrated abrogation of reactivity of serum or CSF of 3 patients (those shown in Table 1) with brain of DPPX-null mice indicating that patients' antibodies were directed only against DPPX, and 1 patient had additional antibodies against a protein of unknown identity (FIG. 4H).

3. Gable M S, Sheriff H, Dalmau J, Tilley D H, Glaser C A. The Frequency of Autoimmune N-Methyl-D-Aspartate Receptor Encephalitis Surpasses That of Individual Viral Etiologies in Young Individuals Enrolled in the California Encephalitis Project. *Clin Infect Dis* 2012.
4. Gable M S, Gavali S, Radner A, Tilley D H, Lee B, Dyner L, et al. Anti-NMDA receptor encephalitis: report of ten cases and comparison with viral encephalitis. *Eur J Clin Microbiol Infect Dis* 2009; 28:1421-1429.

TABLE 1

Clinical features, treatment, and outcome

| Sex, age | Initial symptoms | Main symptoms | Other | Initial CSF | Brain MRI | EEG | Treatment (ordered chronologically) | Outcome (duration follow-up) |
|---|---|---|---|---|---|---|---|---|
| M, 61 | Abdominal pain, diarrhea, depression, aggression, withdrawal | Paranoid delusions, visual hallucinations, mutism, resting tremor, myoclonus, exaggerated startle response. | Decreased level of consciousness, able to track, but not follow commands, orofacial-dyskinesias. Suspected seizures | WBC 117, protein 82, normal glucose, IgG index 1.36, no OCB. Over the course of 1 year: WBC (1-28), protein (34-111), IgG index (0.92-1.36) | Multiple MRIs: Non-specific patchy periventricular and subcortical white matter T2/FLAIR increased signal. | Video EEG: diffuse slowing, poor organization; no epileptic activity | IV methylprednisolone, oral steroids: substantial improvement, but relapsed with steroid taper. IVIg: mild improvement. Rituximab: mild improvement. Plasma exchange: substantial improvement. Cyclophosphamide: steady, but incomplete improvement | Able to return home 15 months after symptom onset. Currently completing the 6$^{th}$ monthly cycle of cyclophosphamide. Oriented to person, place and time, able to follow simple conversations. Occasional episodes of agitation. Persistent deficits in executive functioning, attention/concentration, visual-spatial functioning. (FU = 21 months) |
| F, 45 | Diarrhea, 30 kg weight loss, memory deficit, insomnia, anxiety | Agitation, paranoia hallucinations, anxiety, insomnia. Recurrent generalized seizures, episodes of status epilepticus. Myoclonus, coarse resting tremor | Decreased level of consciousness, hyperreflexia, orofacial movements, horizontal nystagmus. ANA > 2560 | WBC 15, normal protein; normal glucose; positive OCB. | Multiple MRIs Normal | Background with intermittent generalized theta, delta. PLEDS. | IV methylprednisolone: no response. IVIg: slow improvement. Rituximab: accelerated improvement (remains on periodic Rituximab). | Good. Mild transient relapse when rituximab was skipped. Living independently, normal cognition. Dependent on Rituximab. (FU = 49 months) |
| F, 58 | none | Hallucinations, decreased speech, parasomnias, myoclonus, tremor, unsteady gait. | Psychosis (admitted to psychiatry). Clinically suspected seizures. Congenital nystagmus. Single stranded DNA antibodies; no antibodies to dsDNA. | WBC 11, protein 50, increased IgG index, positive OCB. | Multiple MRIs: non-specific white matter changes. One showing non-acute but new right frontal infarction (biopsy = resolving infarction without vasculitis) | slow background activity | Prednisone: improvement (relapses at several tapers). IVIg and rituximab: no clear effect. Cyclophosphamide: 1 cycle (no further cycles due to cryptococcal pneumonia). Plasma exchange: partial improvement. | Alert, attentive, fully oriented, normal short-term memory, knows current events. No tremor, myoclonus, or hallucinations. Walks with a slightly wide base. (FU = 68 months) |

OCB: oligoclonal bands;
FU: follow-up

REFERENCES

1. Lancaster E, Martinez-Hernandez E, Dalmau J. Encephalitis and antibodies to synaptic and neuronal cell surface proteins. *Neurology* 2011; 77:179-189.
2. Frechette E S, Zhou L, Galetta S L, Chen L, Dalmau J. Prolonged follow-up and CSF antibody titers in a patient with anti-NMDA receptor encephalitis. *Neurology* 2011; 76:S64-S66.
5. Nadal M S, Ozaita A, Amarillo Y, Vega-Saenz de M E, Ma Y, Mo W, et al. The CD26-related dipeptidyl aminopeptidase-like protein DPPX is a critical component of neuronal A-type K+ channels. *Neuron* 2003; 37:449-461.
6. Jerng H H, Pfaffinger P J, Covarrubias M. Molecular physiology and modulation of somatodendritic A-type potassium channels. *Mol Cell Neurosci* 2004; 27:343-369.
7. Lai M, Huijbers M G, Lancaster E, Graus F, Bataller L, Balice-Gordon R, et al. Investigation of LGI1 as the antigen in limbic encephalitis previously attributed to potassium channels: a case series. *Lancet Neurol* 2010; 9:776-785.
8. Irani S R, Alexander S, Waters P, Kleopa K A, Pettingill P, Zuliani L, et al. Antibodies to Kv1 potassium channel-complex proteins leucine-rich, glioma inactivated 1 protein and contactin-associated protein-2 in limbic encephalitis, Morvan's syndrome and acquired neuromyotonia. *Brain* 2010; 133:2734-2748.
9. Kim J, Nadal M S, Clemens A M, Baron M, Jung S C, Misumi Y, et al. Kv4 accessory protein DPPX (DPP6) is a critical regulator of membrane excitability in hippocampal CA1 pyramidal neurons. *J Neurophysiol* 2008; 100:1835-1847.
10. Nadal M S, Amarillo Y, Vega-Saenz de M E, Rudy B. Evidence for the presence of a novel Kv4-mediated A-type K(+) channel-modifying factor. *J Physiol* 2001; 537:801-809.
11. Zagha E, Ozaita A, Chang S Y, Nadal M S, Lin U, Saganich M J, et al. DPP10 modulates Kv4-mediated A-type potassium channels. *J Biol Chem* 2005; 280:18853-18861.
12. Qi S Y, Riviere P J, Trojnar J, Junien J L, Akinsanya K O. Cloning and characterization of dipeptidyl peptidase 10, a new member of an emerging subgroup of serine proteases. *Biochem J* 2003; 373:179-189.
13. Wada K, Yokotani N, Hunter C, Doi K, Wenthold R J, Shimasaki S. Differential expression of two distinct forms of mRNA encoding members of a dipeptidyl aminopeptidase family. *Proc Natl Acad Sci USA* 1992; 89:197-201.
14. Nadal M S, Amarillo Y, Vega-Saenz de M E, Rudy B. Differential characterization of three alternative spliced isoforms of DPPX. *Brain Res* 2006; 1094:1-12.
15. Kaulin Y A, De Santiago-Castillo J A, Rocha C A, Nadal M S, Rudy B, Covarrubias M. The dipeptidyl-peptidase-like protein DPP6 determines the unitary conductance of neuronal Kv4.2 channels. *J Neurosci* 2009; 29:3242-3251.
16. Singh B, Ogiwara I, Kaneda M, Tokonami N, Mazaki E, Baba K, et al. A Kv4.2 truncation mutation in a patient with temporal lobe epilepsy. *Neurobiol Dis* 2006; 24:245-253.
17. Rönspeck W, Brinckmann R, Egner R, Gebauer F, Winkler D, Jekow P, et. al. Peptide based adsorbers for therapeutic immunoadsorption. *Ther Apher Dial* 2003 February; 7(1):91-7.
18. Ances B M, Vitaliani R, Taylor R A, Liebeskind D S, Voloschin A, Houghton D J, et al. Treatment-responsive limbic encephalitis identified by neuropil antibodies: MRI and PET correlates. *Brain* 2005; 128:1764-1777.
19. Buchhalter J R, Dichter M A. Electrophysiological comparison of pyramidal and stellate nonpyramidal neurons in dissociated cell culture of rat hippocampus. *Brain Res Bull* 1991; 26:333-338.
20. Strader M B, Tabb D L, Hervey W J, Pan C, Hurst G B. Efficient and specific trypsin digestion of microgram to nanogram quantities of proteins in organic-aqueous solvent systems. *Anal Chem* 2006; 78(1):125-134.
21. Dalmau J, Gleichman A J, Hughes E G, Rossi J E, Peng X, Lai M, et al. Anti-NMDA-receptor encephalitis: case series and analysis of the effects of antibodies. *Lancet Neurol* 2008; 7:1091-1098.
22. Clark B D, Kwon E, Maffie J, Jeong H Y, Nadal M, Strop P, Rudy B. DPP6 Localization in Brain Supports Function as a Kv4 Channel Associated Protein. *Front Mol Neurosci* 2008; 1:8.
23. Lai M, Hughes E G, Peng X, Zhou L, Gleichman A J, Shu H, et al. AMPA receptor antibodies in limbic encephalitis alter synaptic receptor location. *Ann Neurol* 2009; 65:424-434.

The invention claimed is:

1. A method for determining the presence or absence of an autoantibody in a sample obtained from a subject, wherein the autoantibody is capable of binding to a protein dipeptidyl-peptidase-like protein-6 (DPPX), comprising:
   a. contacting the sample with the protein DPPX, and
   b. determining the presence or absence of the autoantibody in the sample,
   wherein the protein DPPX comprises:
      (i) the sequence according to SEQ ID NO: 1, 2, 3, or 4,
      (ii) a polypeptide having the extracellular domain according to SEQ ID NO: 2 and the intracellular and transmembrane domains according to SEQ ID NO: 3 or 4,
      (iii) a sequence with at least 90% sequence identity to SEQ ID NO: 1, 2, 3, or 4, or
      (iv) a sequence with at least 90% sequence identity to the polypeptide having the extracellular domain according to SEQ ID NO: 2 and intracellular and transmembrane domains according to SEQ ID NO: 3 or 4.

2. The method of claim 1, wherein the protein DPPX comprises the sequence according to SEQ ID NO: 1 or the sequence with at least 90% sequence identity to SEQ ID NO:1.

3. The method of claim 1, wherein the protein DPPX comprises the sequence according to SEQ ID NO: 2 or the sequence with at least 90% sequence identity to SEQ ID NO. 2.

4. The method of claim 1, wherein the protein DPPX comprises the sequence according to SEQ ID NO: 3 or the sequence with at least 90% sequence identity to SEQ ID NO: 3.

5. The method of claim 1, wherein the protein DPPX comprises the sequence according to SEQ ID NO: 4 or the sequence with at least 90% sequence identity to SEQ ID NO:4.

6. The method of claim 1, wherein the protein DPPX comprises the polypeptide having the extracellular domain according to SEQ ID NO: 2 and the intracellular and transmembrane domains according to SEQ ID NO: 3 or 4, or the sequence with at least 90% sequence identity to the polypeptide having the extracellular domain according to SEQ ID NO: 2 and intracellular and transmembrane domains according to SEQ ID NO: 3 or 4.

7. The method of claim 1, wherein the protein DPPX comprises further amino acids at its N-terminus or C-terminus to facilitate purification of the protein.

8. The method of claim 1, wherein the protein DPPX is linked to a reporter-molecule or a solid phase.

9. The method according to claim 1, wherein the binding of the autoantibody from the sample to the protein DPPX is detected with an immunofluorescence-test, protein microarray, ELISA, luminiscence-test, blot, radioimmune test, western blot or dot blot.

10. The method of claim 1, wherein the sample is from a subject having or suspected to have an autoimmune disease.

11. The method of claim 1, wherein the protein DPPX is coated on a medical device.

12. The method of claim 1, wherein the sample is a serum sample or a cerebrospinal fluid (CSF) sample.

13. The method of claim 1, wherein the protein DPPX comprises SEQ ID NO:1.

* * * * *